United States Patent
Alden et al.

(10) Patent No.: US 7,316,700 B2
(45) Date of Patent: *Jan. 8, 2008

(54) SELF OPTIMIZING LANCING DEVICE WITH ADAPTATION MEANS TO TEMPORAL VARIATIONS IN CUTANEOUS PROPERTIES

(75) Inventors: Don Alden, Sunnyvale, CA (US); Dominique M. Freeman, La Honda, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 596 days.

This patent is subject to a terminal disclaimer.

(21) Appl. No.: 10/220,828

(22) PCT Filed: Jun. 12, 2002

(86) PCT No.: PCT/US02/19053

§ 371 (c)(1),
(2), (4) Date: Sep. 4, 2002

(87) PCT Pub. No.: WO02/100251

PCT Pub. Date: Dec. 19, 2002

(65) Prior Publication Data

US 2003/0233112 A1   Dec. 18, 2003

(51) Int. Cl.
*A61B 17/32*   (2006.01)
(52) U.S. Cl. .................. 606/181; 600/583
(58) Field of Classification Search ........ 606/181–186, 606/156, 169; 600/557, 573, 583; 604/46, 604/197–198
See application file for complete search history.

(56) References Cited

U.S. PATENT DOCUMENTS

| | | | |
|---|---|---|---|
| 2,714,890 A | 8/1955 | Vang | 128/305 |
| 3,086,288 A | 4/1963 | Balamuth et al. | 30/272 |
| 3,208,452 A | 9/1965 | Stern | 128/315 |
| 3,358,689 A | 12/1967 | Higgins | 128/329 |
| 3,494,358 A | 2/1970 | Grossenbacher | 128/218 |
| 3,626,929 A | 12/1971 | Sanz | 128/2 R |
| 3,673,475 A | 6/1972 | Britton, Jr. | 318/122 |
| 3,742,954 A | 7/1973 | Strickland | 128/302 |
| 3,832,776 A | 9/1974 | Sawyer | 30/272 |
| 3,953,172 A | 4/1976 | Shapiro et al. | 23/230 |
| 4,077,406 A | 3/1978 | Sandhage et al. | 128/217 |
| 4,154,228 A | 5/1979 | Feldstein et al. | 128/329 |
| 4,203,446 A | 5/1980 | Höfert et al. | 128/329 |
| 4,223,674 A | 9/1980 | Fluent et al. | 128/217 |
| 4,224,125 A | 9/1980 | Nakamura | 204/195 B |
| 4,230,118 A | 10/1980 | Holman et al. | 128/314 |
| 4,338,174 A | 7/1982 | Tamura | 204/195 |

(Continued)

FOREIGN PATENT DOCUMENTS

DE   4420232   12/1995

(Continued)

*Primary Examiner*—Michael J. Hayes
*Assistant Examiner*—Victor Nguyen
(74) *Attorney, Agent, or Firm*—Heller Ehrman LLP; Paul Davis

(57) ABSTRACT

A lancing device, an embodiment of which controls the advancement and retraction of a lancet by monitoring the position of the lancet in conjunction with a lancet controller which incorporates a feedback loop for modulating the lancet driver to follow a predetermined tissue lancing profile.

19 Claims, 7 Drawing Sheets

U.S. PATENT DOCUMENTS

| | | | |
|---|---|---|---|
| 4,340,669 A | 7/1982 | Bauer | 435/14 |
| 4,353,984 A | 10/1982 | Yamada | 435/14 |
| 4,356,826 A | 11/1982 | Kubota | 128/630 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,420,564 A | 12/1983 | Tsuji | 435/288 |
| 4,426,451 A | 1/1984 | Columbus | 436/518 |
| 4,426,884 A | 1/1984 | Polchaninoff | 73/172 |
| 4,449,529 A | 5/1984 | Burns et al. | 128/314 |
| 4,462,405 A | 7/1984 | Ehrlich | 128/329 |
| 4,469,110 A | 9/1984 | Slama | 128/770 |
| 4,517,978 A | 5/1985 | Levin | 128/314 |
| 4,518,384 A | 5/1985 | Tarello et al. | 604/61 |
| 4,535,773 A | 8/1985 | Yoon | 604/51 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,590,411 A | 5/1986 | Kelly | 318/687 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia et al. | 128/770 |
| 4,637,393 A | 1/1987 | Ray | 128/305 |
| 4,637,403 A | 1/1987 | Garcia et al. | 128/770 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,653,513 A | 3/1987 | Dombrowski | 128/765 |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,750,489 A | 6/1988 | Berkman et al. | 128/314 |
| 4,758,323 A | 7/1988 | Davis | 204/403 |
| 4,787,398 A | 11/1988 | Garcia et al. | 128/770 |
| 4,794,926 A | 1/1989 | Munsch et al. | 128/314 |
| 4,814,142 A | 3/1989 | Gleisner | 422/56 |
| 4,814,661 A | 3/1989 | Ratzlaff | 310/328 |
| 4,820,010 A | 4/1989 | Scifres | 385/43 |
| 4,820,399 A | 4/1989 | Senda | 204/403 |
| 4,823,806 A | 4/1989 | Bajada | 128/744 |
| 4,824,639 A | 4/1989 | Hildenbrand | 422/56 |
| RE32,922 E | 5/1989 | Levin et al. | 128/314 |
| 4,827,763 A | 5/1989 | Bourland | 73/172 |
| 4,830,959 A | 5/1989 | McNeil | 435/53 |
| 4,836,904 A | 6/1989 | Armstrong | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birth | 204/409 |
| 4,911,794 A | 3/1990 | Parce | 204/1 T |
| 4,920,977 A | 5/1990 | Haynes | 128/770 |
| 4,924,879 A | 5/1990 | O'Brien | 128/770 |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,995,402 A | 2/1991 | Smith et al. | 128/771 |
| 4,999,582 A | 3/1991 | Parks | 324/438 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413 |
| 5,026,388 A | 6/1991 | Ingalz | 606/182 |
| 5,029,583 A | 7/1991 | Meserol et al. | 128/633 |
| 5,035,704 A | 7/1991 | Lambert et al. | 606/182 |
| 5,047,044 A | 9/1991 | Smith et al. | 606/182 |
| 5,054,499 A | 10/1991 | Swierczek | 128/770 |
| 5,059,789 A | 10/1991 | Salcudean | 435/4 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,097,810 A | 3/1992 | Fishman et al. | 128/743 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,145,565 A | 9/1992 | Kater et al. | 204/153.1 |
| 5,152,775 A | 10/1992 | Ruppert | 606/182 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | 24/146 |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,188,118 A | 2/1993 | Terwilliger | 128/753 |
| 5,189,751 A | 3/1993 | Giuliani et al. | 15/22.1 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,215,587 A * | 6/1993 | McConnellogue et al. | 118/699 |
| 5,216,597 A | 6/1993 | Beckers | 364/413.02 |
| 5,217,480 A | 6/1993 | Haber | 606/182 |
| 5,222,504 A | 6/1993 | Solomon | 128/744 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |

| | | | |
|---|---|---|---|
| 5,256,998 A | 10/1993 | Becker ................ 335/229 |
| 5,264,103 A | 11/1993 | Yoshioka ............. 204/403 |
| 5,264,105 A | 11/1993 | Gregg ................. 204/403 |
| 5,264,106 A | 11/1993 | McAleer .............. 204/403 |
| 5,266,179 A | 11/1993 | Nankai ................ 204/401 |
| D342,673 S | 12/1993 | Kataoka et al. ......... 24/147 |
| 5,272,087 A | 12/1993 | El Murr ............... 435/291 |
| 5,277,181 A | 1/1994 | Mendelson ........... 128/633 |
| 5,279,294 A | 1/1994 | Anderson et al. ...... 128/633 |
| 5,282,822 A | 2/1994 | Macors ................ 606/182 |
| 5,286,362 A | 2/1994 | Hoenes ................ 204/403 |
| 5,286,364 A | 2/1994 | Yacynych ............. 204/418 |
| 5,288,636 A | 2/1994 | Pollmann ............. 435/288 |
| 5,304,192 A | 4/1994 | Crouse ................ 606/181 |
| 5,304,193 A | 4/1994 | Zhadanov ............. 606/182 |
| 5,312,590 A | 5/1994 | Gunasingham ........ 422/56 |
| 5,314,441 A | 5/1994 | Cusack ................ 606/182 |
| 5,314,442 A | 5/1994 | Morita ................. 606/182 |
| 5,316,012 A | 5/1994 | Siegal ................. 128/744 |
| 5,316,229 A | 5/1994 | Draghetti ............. 606/171 |
| 5,318,583 A | 6/1994 | Rabenau et al. ....... 606/182 |
| 5,320,607 A | 6/1994 | Ishibashi ............. 604/115 |
| 5,320,808 A | 6/1994 | Holen et al. .......... 422/64 |
| 5,324,302 A | 6/1994 | Crouse ................ 606/181 |
| 5,324,303 A | 6/1994 | Strong ................. 606/181 |
| 5,332,479 A | 7/1994 | Uenoyama .......... 204/153.12 |
| 5,350,392 A | 9/1994 | Purcell ................ 606/182 |
| 5,352,351 A | 10/1994 | White ................. 204/406 |
| 5,354,287 A | 10/1994 | Wacks ................ 604/232 |
| 5,354,447 A | 10/1994 | Uenoyama ........... 204/403 |
| 5,356,420 A | 10/1994 | Czernecki ............ 606/182 |
| 5,360,410 A | 11/1994 | Wacks ................ 604/232 |
| 5,366,469 A | 11/1994 | Steg .................. 606/182 |
| 5,366,470 A | 11/1994 | Ramel ................ 606/183 |
| 5,366,609 A | 11/1994 | White ................. 204/403 |
| 5,368,047 A | 11/1994 | Suzuki et al. ......... 128/765 |
| 5,371,687 A | 12/1994 | Holmes ............... 364/514 |
| 5,375,397 A | 12/1994 | Ferrand ............... 54/66 |
| 5,378,628 A | 1/1995 | Gratzel ............... 435/288 |
| 5,382,346 A | 1/1995 | Uenoyama ........... 204/403 |
| 5,383,885 A | 1/1995 | Bland ................. 606/182 |
| 5,389,534 A | 2/1995 | Gentzkow ............ 435/180 |
| 5,393,903 A | 2/1995 | Gratzel ............... 556/137 |
| 5,395,387 A | 3/1995 | Burns ................. 606/181 |
| 5,397,334 A | 3/1995 | Schenk ............... 606/182 |
| 5,401,376 A | 3/1995 | Foos .................. 204/415 |
| 5,402,798 A | 4/1995 | Swierczek ........... 128/770 |
| 5,405,511 A | 4/1995 | White ................. 204/153.1 |
| 5,407,545 A | 4/1995 | Hirose ................ 204/153.12 |
| 5,407,554 A | 4/1995 | Saurer ................ 204/403 |
| 5,407,818 A | 4/1995 | Gentzkow ............ 435/180 |
| 5,409,583 A | 4/1995 | Yoshioka ............. 204/153.12 |
| 5,410,059 A | 4/1995 | Fraser ................ 546/10 |
| 5,415,169 A | 5/1995 | Siczek et al. ........ 128/653.1 |
| 5,423,847 A | 6/1995 | Strong et al. ......... 606/182 |
| 5,436,161 A | 7/1995 | Bergstrom ........... 435/291 |
| 5,437,999 A | 8/1995 | Diebold .............. 435/288 |
| 5,438,271 A | 8/1995 | White ................. 324/444 |
| 5,443,701 A | 8/1995 | Willner ............... 204/153 |
| 5,445,920 A | 8/1995 | Saito .................. 430/311 |
| D362,719 S | 9/1995 | Kaplan ................ 24/147 |
| 5,454,828 A | 10/1995 | Schraga .............. 606/181 |
| 5,456,875 A | 10/1995 | Lambert .............. 264/328.1 |
| 5,464,418 A | 11/1995 | Schraga .............. 606/182 |
| 5,471,102 A | 11/1995 | Becker ............... 310/50 |
| 5,472,427 A | 12/1995 | Rammler ............. 604/164 |
| 5,474,084 A | 12/1995 | Cunniff .............. 128/744 |
| 5,476,474 A | 12/1995 | Davis ................. 606/182 |
| 5,480,387 A | 1/1996 | Gabriel ............... 604/134 |
| 5,487,748 A | 1/1996 | Marshall ............. 606/182 |
| 5,496,453 A | 3/1996 | Uenoyama ........... 205/777.5 |
| 5,498,542 A | 3/1996 | Corey ................. 435/283.1 |
| 5,507,288 A | 4/1996 | Bocker ............... 128/633 |
| 5,508,171 A | 4/1996 | Walling .............. 205/777.5 |
| 5,509,410 A | 4/1996 | Hill ................... 128/637 |
| 5,510,266 A | 4/1996 | Bonner et al. ........ 436/43 |
| 5,512,159 A | 4/1996 | Yoshioka et al. ..... 204/403 |
| 5,514,152 A | 5/1996 | Smith ................. 606/182 |
| 5,518,006 A | 5/1996 | Mawhirt ............. 128/770 |
| 5,524,636 A | 6/1996 | Sarvazyan ........... 128/774 |
| 5,525,511 A | 6/1996 | D'Costa .............. 435/287.9 |
| 5,527,333 A | 6/1996 | Nikkels .............. 606/182 |
| 5,527,334 A | 6/1996 | Kanner ............... 606/182 |
| 5,529,074 A | 6/1996 | Greenfield ........... 128/744 |
| 5,540,709 A | 7/1996 | Ramel ................ 606/183 |
| 5,543,326 A | 8/1996 | Heller ................ 435/287.9 |
| 5,545,174 A | 8/1996 | Schenk ............... 606/182 |
| 5,547,702 A | 8/1996 | Gleisner .............. 427/2.13 |
| 5,554,166 A | 9/1996 | Lange ................. 606/182 |
| 5,558,834 A | 9/1996 | Chu ................... 422/55 |
| 5,569,286 A | 10/1996 | Peckham ............. 606/181 |
| 5,569,287 A | 10/1996 | Tezuka ............... 606/182 |
| 5,571,132 A | 11/1996 | Mawhirt ............. 606/182 |
| 5,575,403 A | 11/1996 | Charlton et al. ...... 221/31 |
| 5,575,895 A | 11/1996 | Ikeda ................. 204/403 |
| 5,582,697 A | 12/1996 | Ikeda ................. 204/403 |
| 5,584,846 A | 12/1996 | Mawhirt ............. 606/181 |
| 5,593,852 A | 1/1997 | Heller ................ 435/14 |
| 5,609,749 A | 3/1997 | Yamauchi ........... 205/777.5 |
| 5,613,978 A | 3/1997 | Harding .............. 606/181 |
| 5,620,279 A | 4/1997 | Furusawa et al. ..... 204/402 |
| 5,624,537 A | 4/1997 | Turner ................ 204/403 |
| D379,516 S | 5/1997 | Rutter ................ 24/146 |
| 5,628,764 A | 5/1997 | Schraga .............. 606/182 |
| 5,628,765 A | 5/1997 | Morita ................ 606/182 |
| 5,628,890 A | 5/1997 | Carter ................ 204/403 |
| 5,630,986 A | 5/1997 | Charlton et al. ...... 422/64 |
| 5,632,410 A | 5/1997 | Moulton et al. ...... 221/79 |
| 5,640,954 A | 6/1997 | Pfeiffer .............. 128/635 |
| 5,643,306 A | 7/1997 | Schraga .............. 606/182 |
| 5,645,555 A | 7/1997 | Davis ................. 606/182 |
| 5,650,062 A | 7/1997 | Ikeda ................. 205/778 |
| 5,653,863 A | 8/1997 | Genshaw ............ 205/777.5 |
| 5,657,760 A | 8/1997 | Ying et al. .......... 128/660.03 |
| 5,658,444 A | 8/1997 | Black ................. 204/415 |
| 5,662,127 A | 9/1997 | De Vaughn .......... 128/765 |
| 5,662,672 A | 9/1997 | Pambianchi .......... 606/181 |
| 5,676,143 A | 10/1997 | Simonsen ........... 128/633 |
| 5,680,858 A | 10/1997 | Hansen et al. ....... 128/635 |
| 5,680,872 A | 10/1997 | Sesekura ............. 128/760 |
| 5,682,884 A | 11/1997 | Hill ................... 128/637 |
| 5,683,562 A | 11/1997 | Schaffar ............. 204/403 |
| 5,695,947 A | 12/1997 | Guo .................. 435/11 |
| 5,700,695 A | 12/1997 | Yassinzadeh et al. .. 436/180 |
| 5,705,045 A | 1/1998 | Park .................. 204/403 |
| 5,708,247 A | 1/1998 | McAleer ............. 204/403 |
| 5,709,668 A | 1/1998 | Wacks ............... 604/232 |
| 5,709,699 A | 1/1998 | Warner ............... 606/181 |
| 5,710,011 A | 1/1998 | Forrow ............... 435/25 |
| 5,714,390 A | 2/1998 | Hallowitz et al. .... 436/526 |
| 5,720,862 A | 2/1998 | Hamamoto ........... 204/403 |
| 5,720,924 A | 2/1998 | Eikmeier et al. ..... 422/102 |
| D392,391 S | 3/1998 | Douglas .............. 24/225 |
| 5,723,284 A | 3/1998 | Ye .................... 435/4 |
| 5,727,548 A | 3/1998 | Hill ................... 128/637 |
| 5,730,753 A | 3/1998 | Morita ................ 606/181 |
| 5,733,300 A | 3/1998 | Pambianchi ......... 606/181 |
| D393,716 S | 4/1998 | Brenneman .......... 24/147 |
| D393,717 S | 4/1998 | Brenneman .......... 24/147 |
| 5,738,244 A | 4/1998 | Charlton et al. ...... 221/26 |
| 5,741,228 A | 4/1998 | Lambrecht ........... 604/93 |
| 5,741,634 A | 4/1998 | Nozoe ................ 435/4 |
| RE35,803 E | 5/1998 | Lange ................. 606/182 |
| 5,746,217 A | 5/1998 | Erickson ............. 128/760 |
| 5,746,898 A | 5/1998 | Preidel ............... 204/403 |
| 5,755,733 A | 5/1998 | Morita ................ 606/182 |

| | | | | | | | |
|---|---|---|---|---|---|---|---|
| 5,758,643 | A | 6/1998 | Wong et al. ............... 128/632 | 5,922,188 | A | 7/1999 | Ikeda ..................... 204/777.5 |
| 5,759,364 | A | 6/1998 | Charlton ................... 204/403 | RE36,268 | E | 8/1999 | Szuminsky .............. 205/777.5 |
| 5,762,770 | A | 6/1998 | Pritchard .................. 204/403 | 5,933,136 | A | 8/1999 | Brown ........................ 345/327 |
| 5,770,369 | A | 6/1998 | Meade ........................... 435/6 | 5,935,075 | A | 8/1999 | Casscells et al. ........... 600/474 |
| 5,772,586 | A | 6/1998 | Heinonen .................. 600/300 | 5,938,679 | A | 8/1999 | Freeman et al. ............. 606/181 |
| 5,772,677 | A | 6/1998 | Mawhirt ..................... 600/181 | 5,942,102 | A | 8/1999 | Hodges ...................... 205/775 |
| 5,773,270 | A | 6/1998 | D'Orazio ................... 435/177 | 5,951,300 | A | 9/1999 | Brown ........................ 434/236 |
| 5,776,157 | A | 7/1998 | Thorne et al. .............. 606/182 | 5,951,492 | A | 9/1999 | Douglas ..................... 600/583 |
| 5,776,719 | A | 7/1998 | Douglas ....................... 435/28 | 5,951,582 | A | 9/1999 | Thorne et al. .............. 606/182 |
| 5,782,770 | A | 7/1998 | Mooradian ................. 600/476 | 5,951,836 | A | 9/1999 | McAleer ..................... 204/403 |
| 5,782,852 | A | 7/1998 | Foggia ....................... 606/182 | 5,954,738 | A | 9/1999 | LeVaughn .................. 606/181 |
| 5,788,651 | A | 8/1998 | Weilandt .................... 600/567 | 5,956,501 | A | 9/1999 | Brown ..................... 395/500.32 |
| 5,788,652 | A | 8/1998 | Rahn .......................... 600/577 | 5,958,199 | A | 9/1999 | Miyamoto ................... 204/403 |
| 5,794,219 | A | 8/1998 | Brown ........................... 705/37 | 5,960,403 | A | 9/1999 | Brown ........................... 705/2 |
| 5,795,725 | A | 8/1998 | Buechler .................... 435/7.1 | 5,964,718 | A | 10/1999 | Duchon ...................... 600/583 |
| 5,795,774 | A | 8/1998 | Matsumoto ............. 435/287.9 | 5,965,380 | A | 10/1999 | Heller .......................... 435/14 |
| 5,797,940 | A | 8/1998 | Mawhirt ..................... 606/167 | 5,968,063 | A | 10/1999 | Chu et al. ................... 606/185 |
| 5,797,942 | A | 8/1998 | Schraga ...................... 606/182 | 5,971,941 | A * | 10/1999 | Simons et al. ............... 600/573 |
| 5,798,030 | A | 8/1998 | Raguse ....................... 204/403 | 5,972,199 | A | 10/1999 | Heller ..................... 205/777.5 |
| 5,798,031 | A | 8/1998 | Charlton ..................... 204/403 | 5,972,715 | A | 10/1999 | Celentano ................... 436/164 |
| 5,800,781 | A | 9/1998 | Gavin et al. .................. 422/73 | 5,974,124 | A | 10/1999 | Schlueter ................ 379/106.02 |
| 5,801,057 | A | 9/1998 | Smart et al. .................. 436/68 | 5,983,193 | A | 11/1999 | Heinonen ...................... 705/2 |
| 5,807,375 | A | 9/1998 | Gross ...................... 604/890.1 | 5,985,116 | A | 11/1999 | Ikeda ......................... 204/403 |
| 5,810,199 | A | 9/1998 | Charlton et al. .............. 221/31 | 5,985,559 | A | 11/1999 | Brown ........................... 435/6 |
| 8,800,781 | | 9/1998 | Gavin ........................... 422/73 | 5,993,400 | A | 11/1999 | Rincoe ....................... 600/595 |
| 5,820,551 | A | 10/1998 | Hill ............................. 600/347 | 5,997,476 | A | 12/1999 | Brown ........................ 600/300 |
| 5,822,715 | A | 10/1998 | Worthington ................. 702/19 | 5,997,561 | A | 12/1999 | Bocker et al. ............... 606/182 |
| 5,823,973 | A | 10/1998 | Racchini et al. ............. 600/573 | 5,997,817 | A | 12/1999 | Crismore ....................... 422/58 |
| 5,824,491 | A | 10/1998 | Priest ............................ 435/28 | 5,997,818 | A | 12/1999 | Hacker ........................ 422/681 |
| 5,828,943 | A | 10/1998 | Brown ........................ 434/236 | 6,001,067 | A | 12/1999 | Shults .......................... 600/584 |
| 5,830,219 | A | 11/1998 | Bird et al. ................... 606/130 | 6,015,392 | A | 1/2000 | Douglas ..................... 600/583 |
| 5,832,448 | A | 11/1998 | Brown ........................... 705/2 | 6,020,110 | A | 2/2000 | Williams ..................... 430/315 |
| 5,840,020 | A | 11/1998 | Heinonen ................... 600/309 | 6,022,324 | A | 2/2000 | Skinner ....................... 600/566 |
| 5,840,171 | A | 11/1998 | Birch .......................... 205/335 | 6,022,366 | A | 2/2000 | Schraga ...................... 606/181 |
| 5,846,490 | A | 12/1998 | Yokota et al. ................. 422/66 | 6,023,686 | A | 2/2000 | Brown ........................... 705/37 |
| 5,849,174 | A | 12/1998 | Sanghera .................... 205/775 | 6,027,459 | A | 2/2000 | Shain et al. .................. 600/573 |
| 5,853,373 | A | 12/1998 | Griffith ....................... 600/554 | 6,030,399 | A | 2/2000 | Ignotz ......................... 606/167 |
| 5,854,074 | A | 12/1998 | Charlton et al. .............. 436/46 | 6,030,827 | A | 2/2000 | Davis ......................... 435/287 |
| D403,975 | S | 1/1999 | Douglas ........................ 10/81 | 6,032,119 | A | 2/2000 | Brown ........................... 705/2 |
| 5,855,801 | A | 1/1999 | Lin et al. ....................... 216/2 | 6,033,421 | A | 3/2000 | Theiss ........................... 66/186 |
| 5,857,983 | A | 1/1999 | Douglas ..................... 600/538 | 6,033,866 | A | 3/2000 | Guo ............................... 435/14 |
| 5,860,922 | A | 1/1999 | Gordon et al. .............. 600/431 | 6,036,924 | A | 3/2000 | Simons et al. ............... 422/100 |
| 5,863,800 | A | 1/1999 | Eikmeier et al. .............. 436/48 | 6,041,253 | A | 3/2000 | Kost .............................. 604/20 |
| 5,866,353 | A | 2/1999 | Berneth ........................ 435/26 | 6,048,352 | A | 4/2000 | Douglas et al. ............. 606/181 |
| 5,868,135 | A | 2/1999 | Kaufman .................... 128/630 | D424,696 | S | 5/2000 | Ray ............................. 24/169 |
| 5,868,772 | A | 2/1999 | LeVaughn ................... 606/181 | 6,056,701 | A | 5/2000 | Duchon ....................... 600/583 |
| 5,869,972 | A | 2/1999 | Birch .......................... 324/439 | 6,060,327 | A | 5/2000 | Keen ........................... 436/518 |
| 5,871,494 | A * | 2/1999 | Simons et al. .............. 606/181 | 6,061,128 | A | 5/2000 | Zweig ....................... 356/243.4 |
| 5,872,713 | A | 2/1999 | Douglas ........................ 702/85 | 6,063,039 | A | 5/2000 | Cunningham ............... 600/573 |
| 5,873,887 | A | 2/1999 | King ........................... 606/182 | 6,066,103 | A | 5/2000 | Duchon ...................... 600/583 |
| 5,876,957 | A | 3/1999 | Douglas ........................ 435/26 | 6,066,296 | A | 5/2000 | Brady ........................... 422/63 |
| 5,879,163 | A | 3/1999 | Brown ........................ 434/236 | 6,067,463 | A | 5/2000 | Jeng ............................ 600/336 |
| 5,879,310 | A | 3/1999 | Sopp ........................... 600/578 | 6,068,615 | A | 5/2000 | Brown ........................ 604/207 |
| 5,879,311 | A | 3/1999 | Duchon et al. .............. 600/583 | D426,638 | S | 6/2000 | Ray ............................. 24/169 |
| 5,879,373 | A | 3/1999 | Roper ........................ 606/344 | 6,071,249 | A | 6/2000 | Cunningham ............... 600/578 |
| 5,880,829 | A | 3/1999 | Kauhaniemi et al. ........ 356/246 | 6,071,250 | A | 6/2000 | Douglas ...................... 600/583 |
| 5,882,494 | A | 3/1999 | van Antwerp .............. 204/403 | 6,071,251 | A | 6/2000 | Cunningham ............... 600/584 |
| 5,885,211 | A | 3/1999 | Eppstein et al. ............. 600/309 | 6,071,294 | A * | 6/2000 | Simons et al. ............... 606/181 |
| 5,887,133 | A | 3/1999 | Brown ...................... 395/200.3 | 6,074,360 | A | 6/2000 | Haar et al. ..................... 604/57 |
| RE36,191 | E | 4/1999 | Solomon ..................... 395/308 | 6,077,408 | A | 6/2000 | Miyamoto ................... 204/403 |
| 5,891,053 | A | 4/1999 | Sesekura .................... 600/583 | 6,080,172 | A | 6/2000 | Fujiwara .................... 606/166 |
| 5,893,870 | A | 4/1999 | Talen ......................... 606/201 | 6,083,710 | A | 7/2000 | Heller ........................... 435/14 |
| 5,897,493 | A | 4/1999 | Brown ........................ 600/300 | 6,086,545 | A | 7/2000 | Roe ............................. 600/570 |
| 5,899,855 | A | 5/1999 | Brown ........................ 600/301 | 6,086,562 | A | 7/2000 | Jacobsen .................... 604/156 |
| 5,900,130 | A | 5/1999 | Benvegnu ................... 204/453 | 6,090,078 | A | 7/2000 | Erskine ....................... 604/198 |
| 5,906,921 | A | 5/1999 | Ikeda ............................ 435/25 | 6,093,146 | A | 7/2000 | Filangeri .................... 600/300 |
| D411,619 | S | 6/1999 | Duchon ........................ 24/146 | 6,093,156 | A | 7/2000 | Cunningham et al. ...... 600/573 |
| 5,913,310 | A | 6/1999 | Brown ........................ 128/897 | 6,101,478 | A | 8/2000 | Brown ........................... 705/2 |
| 5,916,156 | A | 6/1999 | Hildenbrand ............... 600/347 | 6,103,033 | A | 8/2000 | Say ............................ 156/73.1 |
| 5,916,229 | A | 6/1999 | Evans ......................... 606/171 | 6,107,083 | A | 8/2000 | Collins ........................ 435/288 |
| 5,916,230 | A | 6/1999 | Brenneman ................. 606/172 | 6,113,578 | A | 9/2000 | Brown ........................ 604/207 |
| 5,918,603 | A | 7/1999 | Brown ........................ 128/897 | 6,117,630 | A | 9/2000 | Reber et al. .................... 435/4 |
| 5,921,963 | A | 7/1999 | Erez ........................... 604/192 | 6,120,462 | A | 9/2000 | Hibner et al. ............... 600/566 |

| Patent No. | Kind | Date | Inventor | Class |
|---|---|---|---|---|
| 6,120,676 | A | 9/2000 | Heller | 205/777.5 |
| 6,121,009 | A | 9/2000 | Heller | 435/14 |
| 6,122,536 | A | 9/2000 | Sun | 600/341 |
| 6,129,823 | A | 10/2000 | Hughes | 204/403.01 |
| 6,132,449 | A | 10/2000 | Lum et al. | 606/181 |
| 6,133,837 | A | 10/2000 | Riley | 340/573.1 |
| 6,134,461 | A | 10/2000 | Say | 600/345 |
| 6,136,013 | A | 10/2000 | Marshall et al. | 606/167 |
| 6,139,562 | A | 10/2000 | Mauze et al. | 606/171 |
| 6,143,164 | A | 11/2000 | Heller et al. | 205/777.5 |
| 6,144,837 | A | 11/2000 | Quy | 434/307 R |
| 6,151,586 | A | 11/2000 | Brown | 705/14 |
| 6,152,942 | A | 11/2000 | Brenneman et al. | 606/181 |
| 6,153,069 | A | 11/2000 | Pottgen | 204/403 |
| RE36,991 | E | 12/2000 | Yamamoto | 204/403 |
| 6,155,267 | A | 12/2000 | Nelson | 128/899 |
| 6,155,992 | A | 12/2000 | Henning et al. | 600/583 |
| 6,156,051 | A | 12/2000 | Schraga | 606/181 |
| 6,157,442 | A | 12/2000 | Raskas | 356/39 |
| 6,159,424 | A | 12/2000 | Kauhaniemi et al. | 422/63 |
| 6,161,095 | A | 12/2000 | Brown | 705/2 |
| 6,162,611 | A | 12/2000 | Heller | 435/14 |
| 6,167,362 | A | 12/2000 | Brown | 703/11 |
| 6,167,386 | A | 12/2000 | Brown | 705/37 |
| 6,168,563 | B1 | 1/2001 | Brown | 600/301 |
| 6,171,325 | B1 | 1/2001 | Mauze et al. | 356/446 |
| 6,175,752 | B1 | 1/2001 | Say | 600/345 |
| 6,176,865 | B1 | 1/2001 | Mauze et al. | 606/171 |
| 6,177,000 | B1 | 1/2001 | Peterson | 205/777.5 |
| 6,183,489 | B1 | 2/2001 | Douglas et al. | 606/181 |
| 6,186,145 | B1 | 2/2001 | Brown | 128/897 |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,193,673 | B1 | 2/2001 | Viola et al. | 600/568 |
| 6,194,900 | B1 | 2/2001 | Freeman | 324/321 |
| 6,197,257 | B1 | 3/2001 | Raskas | 422/82.05 |
| 6,203,504 | B1 | 3/2001 | Latterell et al. | 600/576 |
| 6,206,841 | B1 | 3/2001 | Cunningham et al. | 600/584 |
| 6,210,272 | B1 | 4/2001 | Brown | 463/1 |
| 6,210,420 | B1 | 4/2001 | Mauze et al. | 606/182 |
| 6,210,421 | B1 | 4/2001 | Böcker et al. | 606/182 |
| 6,212,417 | B1 | 4/2001 | Ikeda | 204/403.14 |
| 6,214,804 | B1 | 4/2001 | Felgner | 514/44 |
| 6,221,238 | B1 | 4/2001 | Grundig | 205/777.5 |
| 6,225,078 | B1 | 5/2001 | Ikeda | 435/25 |
| 6,228,100 | B1 | 5/2001 | Schraga | 606/183 |
| 6,230,501 | B1 | 5/2001 | Bailey | 62/51.1 |
| 6,231,531 | B1 | 5/2001 | Lum et al. | 601/46 |
| 6,233,471 | B1 | 5/2001 | Berner et al. | 600/345 |
| 6,233,539 | B1 | 5/2001 | Brown | 703/11 |
| 6,240,393 | B1 | 5/2001 | Brown | 705/1 |
| 6,241,862 | B1 | 6/2001 | McAleer | 204/403 |
| 6,245,060 | B1 | 6/2001 | Loomis | 606/9 |
| 6,246,992 | B1 | 6/2001 | Brown | 705/2 |
| 6,248,065 | B1 | 6/2001 | Brown | 600/300 |
| 6,251,260 | B1 | 6/2001 | Heller | 205/777.5 |
| 6,254,831 | B1 | 7/2001 | Barnard | 422/82.08 |
| 6,256,533 | B1 | 7/2001 | Vuzhakov | 604/21 |
| 6,258,229 | B1 | 7/2001 | Winarta | 204/403 |
| 6,258,254 | B1 | 7/2001 | Miyamoto | 205/777.5 |
| 6,261,241 | B1 | 7/2001 | Burbank et al. | 600/564 |
| 6,261,245 | B1 | 7/2001 | Kawai et al. | 600/576 |
| 6,268,161 | B1 | 7/2001 | Han | 435/14 |
| 6,270,455 | B1 | 8/2001 | Brown | 600/300 |
| 6,270,637 | B1 | 8/2001 | Crismore | 204/403 |
| 6,272,359 | B1 | 8/2001 | Kivela | 455/567 |
| 6,281,006 | B1 | 8/2001 | Heller | 435/287.9 |
| 6,283,926 | B1 | 9/2001 | Cunningham et al. | 600/573 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |
| 6,285,454 | B1 | 9/2001 | Douglas et al. | 356/446 |
| 6,290,683 | B1 | 9/2001 | Erez | 604/273 |
| 6,294,897 | B1 | 9/2001 | Champlin | 320/153 |
| 6,295,506 | B1 | 9/2001 | Heinonen | 702/104 |
| 6,299,757 | B1 | 10/2001 | Feldman | 205/775 |
| 6,302,844 | B1 | 10/2001 | Walker | 600/300 |
| 6,302,855 | B1 | 10/2001 | Lav | 600/584 |
| 6,305,804 | B1 | 10/2001 | Rice | 351/221 |
| 6,306,104 | B1 | 10/2001 | Cunningham et al. | 600/573 |
| 6,306,152 | B1 * | 10/2001 | Verdonk et al. | 606/182 |
| 6,306,347 | B1 | 10/2001 | Mason | 422/58 |
| 6,309,535 | B1 | 10/2001 | Williams | 205/777.5 |
| 6,312,612 | B1 | 11/2001 | Sherman | 216/2 |
| 6,315,738 | B1 | 11/2001 | Nishikawa et al. | 600/583 |
| 6,319,210 | B1 | 11/2001 | Douglas et al. | 600/583 |
| 6,322,574 | B1 | 11/2001 | Lloyd | 606/181 |
| 6,329,161 | B1 | 12/2001 | Heller | 435/14 |
| 6,330,426 | B2 | 12/2001 | Brown | 434/307 R |
| 6,331,163 | B1 | 12/2001 | Kaplan | 600/486 |
| 6,332,871 | B1 | 12/2001 | Douglas et al. | 600/583 |
| 6,334,363 | B1 | 1/2002 | Testud | 73/862 |
| 6,334,778 | B1 | 1/2002 | Brown | 434/258 |
| 6,334,856 | B1 | 1/2002 | Allen | 604/191 |
| 6,338,790 | B1 | 1/2002 | Feldman | 205/777.5 |
| 6,349,229 | B1 | 2/2002 | Watanabe | 600/345 |
| 6,350,273 | B1 | 2/2002 | Minagawa | 606/186 |
| 6,350,451 | B1 | 2/2002 | Horn | 424/184.1 |
| 6,352,514 | B1 | 3/2002 | Douglas et al. | 600/583 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri et al. | 606/181 |
| 6,364,890 | B1 | 4/2002 | Lum et al. | 606/181 |
| 6,368,273 | B1 | 4/2002 | Brown | 600/300 |
| 6,375,469 | B1 | 4/2002 | Brown | 434/236 |
| 6,375,627 | B1 | 4/2002 | Mauze et al. | 600/584 |
| 6,379,301 | B1 | 4/2002 | WOrthington | 600/309 |
| 6,379,317 | B1 | 4/2002 | Kintzig et al. | 600/573 |
| 6,379,324 | B1 | 4/2002 | Gartstein | 604/22 |
| 6,379,969 | B1 | 4/2002 | Mauze et al. | 436/68 |
| 6,381,577 | B1 | 4/2002 | Brown | 705/2 |
| 6,387,709 | B1 | 5/2002 | Mason | 436/164 |
| 6,391,005 | B1 | 5/2002 | Lum et al. | 604/117 |
| 6,399,394 | B1 | 6/2002 | Dahm | 436/180 |
| 6,402,701 | B1 | 6/2002 | Kaplan et al. | 600/567 |
| 6,402,704 | B1 | 6/2002 | McMorrow | 600/576 |
| 6,409,740 | B1 | 6/2002 | Kuhr et al. | 606/182 |
| 6,413,410 | B1 | 7/2002 | Hodges | 205/775 |
| 6,413,411 | B1 | 7/2002 | Pottgen | 205/777.5 |
| 6,421,633 | B1 | 7/2002 | Heinonen | 703/11 |
| 6,428,664 | B1 | 8/2002 | Bhullar | 204/403.03 |
| 6,436,256 | B1 | 8/2002 | Williams | 204/403.06 |
| 6,436,721 | B1 | 8/2002 | Kuo | 436/514 |
| 6,440,645 | B1 | 8/2002 | Yon-Hin | 430/322 |
| 6,451,040 | B1 | 9/2002 | Purcell | 606/181 |
| 6,458,258 | B2 | 10/2002 | Taniike | 204/403 |
| 6,461,496 | B1 | 10/2002 | Feldman et al. | 205/777.5 |
| 6,462,162 | B2 | 10/2002 | van Antwerp | 528/77 |
| 6,464,649 | B1 | 10/2002 | Duchon | 600/583 |
| 6,471,903 | B2 | 10/2002 | Sherman | 264/328.1 |
| 6,472,220 | B1 | 10/2002 | Simons et al. | 436/63 |
| 6,475,436 | B1 | 11/2002 | Schabbach | 422/64 |
| 6,477,394 | B2 | 11/2002 | Rice | 600/318 |
| 6,477,424 | B1 | 11/2002 | Thompson | 607/60 |
| 6,484,046 | B1 | 11/2002 | Say | 600/345 |
| 6,485,439 | B1 | 11/2002 | Roe et al. | 600/578 |
| 6,488,891 | B2 | 12/2002 | Mason et al. | 422/58 |
| 6,489,052 | B1 | 12/2002 | Acker | 600/584 |
| 6,491,709 | B2 | 12/2002 | Sharma et al. | 606/181 |
| 6,494,830 | B1 | 12/2002 | Wessel | 600/300 |
| 6,497,845 | B1 | 12/2002 | Sacherer | 422/104 |
| 6,501,404 | B2 | 12/2002 | Walker | 341/143 |
| 6,503,210 | B1 | 1/2003 | Hirao et al. | 600/576 |
| 6,503,231 | B1 | 1/2003 | Prausnitz | 604/272 |
| 6,503,381 | B1 | 1/2003 | Gotoh | 204/403.14 |

| Patent No. | Date | Inventor | Class |
|---|---|---|---|
| 6,506,168 B1 | 1/2003 | Fathallah | 600/578 |
| 6,506,575 B1 | 1/2003 | Knappe et al. | 435/25 |
| 6,508,795 B1 | 1/2003 | Samuelson et al. | 604/113 |
| 6,514,270 B1 | 2/2003 | Schraga | 66/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | 600/583 |
| 6,530,937 B1 | 3/2003 | Schraga | 606/182 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller et al. | 205/777.5 |
| 6,553,244 B1 | 4/2003 | Lesho | 600/309 |
| 6,554,381 B2 | 4/2003 | Locher | 347/7 |
| 6,555,061 B1 | 4/2003 | Leong | 422/58 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say et al. | 600/365 |
| 6,565,808 B2 | 5/2003 | Hudak | 422/58 |
| 6,569,157 B1 | 5/2003 | Shain | 606/12 |
| 657,646 A1 | 6/2003 | Haviland | 435/4 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Iketaki et al. | 205/777.5 |
| 6,576,416 B2 | 6/2003 | Haviland | 435/4 |
| 6,582,573 B2 | 6/2003 | Douglas | 204/403.1 |
| 6,587,705 B1 | 7/2003 | Berner et al. | 600/347 |
| 6,589,260 B1 | 7/2003 | Schmelzeisen-R et al. | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,595,919 B2 | 7/2003 | Berner. | 600/365 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,494 B1 | 8/2003 | Fowler | 600/570 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beatty | 205/792 |
| 6,650,915 B2 | 11/2003 | Routt | 600/319 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-redeker et al. | 600/583 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 66/9 |
| 6,736,777 B2 | 5/2004 | Kim | 600/365 |
| 6,740,215 B1 | 5/2004 | Nakaminami et al. | 204/403.14 |
| 6,743,211 B1 | 6/2004 | PraUsnitz | 604/239 |
| 6,743,635 B2 | 6/2004 | Neel | 436/95 |
| 6,745,750 B2 | 6/2004 | Egler et al. | 435/14 |
| 6,749,618 B2 | 6/2004 | Levaughn | 606/182 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda et al. | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.10 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |

| Patent | Kind | Date | Inventor | Class |
|---|---|---|---|---|
| 6,821,483 | B2 | 11/2004 | Phillips et al. | 422/58 |
| 6,823,750 | B2 | 11/2004 | Hodges | 73/864.72 |
| 6,825,047 | B1 | 11/2004 | Woudenberg | 436/518 |
| 6,827,250 | B2 | 12/2004 | Uhland | 228/110.1 |
| 6,827,829 | B2 | 12/2004 | Kawanaka | 204/403.02 |
| 6,830,551 | B1 | 12/2004 | Uchigaki | 600/584 |
| 6,830,668 | B2 | 12/2004 | Musho | 204/400 |
| 6,830,669 | B2 | 12/2004 | Miyazaki | 204/409 |
| 6,833,540 | B2 | 12/2004 | MacKenzie | 250/214 |
| 6,835,184 | B1 | 12/2004 | Sage | 604/46 |
| 6,835,553 | B2 | 12/2004 | Han | 435/14 |
| 6,837,858 | B2 | 1/2005 | Cunningham | 600/573 |
| 6,837,976 | B2 | 1/2005 | Cai | 204/403.14 |
| 6,837,988 | B2 | 1/2005 | Leong | 205/792 |
| 6,840,912 | B2 | 1/2005 | Kloepfer | 600/583 |
| 6,841,052 | B2 | 1/2005 | Crumly et al. | 204/401 |
| 6,843,254 | B2 | 1/2005 | Tapper | 128/898 |
| 6,847,451 | B2 | 1/2005 | Pugh | 356/436 |
| 6,849,168 | B2 | 2/2005 | Madou et al. | 204/416 |
| 6,849,216 | B2 | 2/2005 | Rappin | 264/134 |
| 6,850,790 | B2 | 2/2005 | Berner | 600/347 |
| 6,869,418 | B2 | 3/2005 | Marano-Ford | 604/192 |
| 6,872,200 | B2 | 3/2005 | Mann | 604/890.1 |
| 6,875,208 | B2 | 4/2005 | Santini | 604/890.1 |
| 6,875,233 | B1 | 4/2005 | Argauer | 606/181 |
| 6,875,613 | B2 | 4/2005 | Shartle | 436/63 |
| 6,878,120 | B2 | 4/2005 | Roe | 600/583 |
| 6,878,251 | B2 | 4/2005 | Hodges | 204/403.14 |
| 6,878,255 | B1 | 4/2005 | Wang | 204/452 |
| 6,878,262 | B2 | 4/2005 | Taniike | 205/777.5 |
| 6,880,968 | B1 | 4/2005 | Haar | 374/131 |
| 6,881,203 | B2 | 4/2005 | Delmore | 604/272 |
| 6,881,322 | B2 | 4/2005 | Tokunaga | 205/775 |
| 6,881,378 | B1 | 4/2005 | Zimmer | 422/58 |
| 6,881,550 | B2 | 4/2005 | Phillips | 435/14 |
| 6,881,551 | B2 | 4/2005 | Heller | 435/14 |
| 6,881,578 | B2 | 4/2005 | Otake | 436/44 |
| 6,882,940 | B2 | 4/2005 | Potts | 702/23 |
| 6,884,592 | B2 | 4/2005 | Matzinger | 435/7.1 |
| 6,885,196 | B2 | 4/2005 | Taniike | 324/444 |
| 6,885,883 | B2 | 4/2005 | Parris | 600/347 |
| 6,887,239 | B2 | 5/2005 | Elstrom | 606/41 |
| 6,887,253 | B2 | 5/2005 | Schraga | 606/181 |
| 6,887,426 | B2 | 5/2005 | Phillips | 422/56 |
| 6,887,709 | B2 | 5/2005 | Leong | 436/8 |
| 6,889,069 | B2 | 5/2005 | Routt | 600/319 |
| 6,890,319 | B1 | 5/2005 | Crocker | 604/131 |
| 6,890,421 | B2 | 5/2005 | Ohara | 205/777.5 |
| 6,890,484 | B2 | 5/2005 | Bautista | 422/58 |
| 6,891,936 | B2 | 5/2005 | Kai | 379/106.02 |
| 6,892,085 | B2 | 5/2005 | McIvor | 600/347 |
| 6,893,396 | B2 | 5/2005 | Schulze | 600/300 |
| 6,893,545 | B2 | 5/2005 | Gotoh | 204/403.5 |
| 6,893,552 | B1 | 5/2005 | Wang | 205/777.5 |
| 6,895,263 | B2 | 5/2005 | Shin | 600/316 |
| 6,895,264 | B2 | 5/2005 | Rice | 600/319 |
| 6,895,265 | B2 | 5/2005 | Silver | 600/345 |
| 6,896,793 | B2 | 5/2005 | Erdosy | 205/775 |
| 6,897,788 | B2 | 5/2005 | Khair | 340/870.16 |
| 6,902,905 | B2 | 6/2005 | Burson | 435/14 |
| 6,904,301 | B2 | 6/2005 | Raskas | 600/310 |
| 6,905,733 | B2 | 6/2005 | Russell | 427/393.5 |
| 6,908,008 | B2 | 6/2005 | Pugh | 221/135 |
| 6,908,535 | B2 | 6/2005 | Rankin | 204/406 |
| 6,908,591 | B2 | 6/2005 | MacPhee | 422/22 |
| 6,908,593 | B1 | 6/2005 | Shartle | 422/58 |
| 6,911,130 | B2 | 6/2005 | Brenneman | 204/400 |
| 6,911,131 | B2 | 6/2005 | Miyazaki | 204/403.14 |
| 6,911,621 | B2 | 6/2005 | Bhullar | 219/121.69 |
| 6,916,410 | B2 | 7/2005 | Katsuki | 204/403 |
| 6,918,918 | B1 | 7/2005 | Schraga | 606/182 |
| 6,922,576 | B2 | 7/2005 | Raskas | 600/316 |
| 6,922,578 | B2 | 7/2005 | Eppstein | 600/347 |
| 6,923,764 | B2 | 8/2005 | Aceti | 600/309 |
| 6,923,894 | B2 | 8/2005 | Huang | 204/403.06 |
| 6,923,936 | B2 | 8/2005 | Swanson | 422/22 |
| 6,924,093 | B2 | 8/2005 | Haviland | 435/4 |
| 6,925,317 | B1 | 8/2005 | Samuels | 600/344 |
| 6,925,393 | B1 | 8/2005 | Kalatz | 702/27 |
| 6,929,649 | B2 | 8/2005 | Pugh | 606/182 |
| 6,929,650 | B2 | 8/2005 | Fukuzawa | 606/182 |
| 6,931,327 | B2 | 8/2005 | Goode | 702/22 |
| 6,931,328 | B2 | 8/2005 | Braig | 702/23 |
| 6,939,310 | B2 | 9/2005 | Matzinger | 600/573 |
| 6,939,312 | B2 | 9/2005 | Hodges | 600/583 |
| 6,939,450 | B2 | 9/2005 | Karinka | 204/409 |
| 6,940,591 | B2 | 9/2005 | Sopp | 356/244 |
| 6,942,518 | B2 | 9/2005 | Liamos | 439/495 |
| 6,942,769 | B2 | 9/2005 | Cheng | 204/400 |
| 6,942,770 | B2 | 9/2005 | Cai | 204/403.04 |
| 6,944,486 | B2 | 9/2005 | Braig | 600/310 |
| 6,945,943 | B2 | 9/2005 | Pugh | 600/584 |
| 6,946,067 | B2 | 9/2005 | Hodges | 205/792 |
| 6,946,098 | B2 | 9/2005 | Miekka | 422/22 |
| 6,946,299 | B2 | 9/2005 | Neel | 436/95 |
| 6,949,111 | B2 | 9/2005 | Schraga | 606/182 |
| 6,949,221 | B2 | 9/2005 | Kiser | 422/56 |
| 6,951,631 | B1 | 10/2005 | Catt | 422/56 |
| 6,951,728 | B2 | 10/2005 | Qian | 435/14 |
| 6,952,603 | B2 | 10/2005 | Gerber | 600/310 |
| 6,952,604 | B2 | 10/2005 | DeNuzzio | 600/345 |
| 6,953,693 | B2 | 10/2005 | Neel | 436/149 |
| 6,954,662 | B2 | 10/2005 | Freger | 600/316 |
| 6,958,072 | B2 | 10/2005 | Schraga | 606/182 |
| 6,958,129 | B2 | 10/2005 | Galen | 422/57 |
| 6,958,809 | B2 | 10/2005 | Sterling | 356/39 |
| 6,959,211 | B2 | 10/2005 | Rule | 600/310 |
| 6,959,247 | B2 | 10/2005 | Neel | 702/19 |
| 6,960,287 | B2 | 11/2005 | Charlton | 205/775 |
| 6,960,289 | B2 | 11/2005 | Hodges | 205/778 |
| 6,964,871 | B2 | 11/2005 | Bell | 436/95 |
| 6,965,791 | B1 | 11/2005 | Hitchcock | 600/345 |
| 6,966,880 | B2 | 11/2005 | Boecker | 600/583 |
| 6,966,977 | B2 | 11/2005 | Hasegawa | 204/403.07 |
| 6,967,105 | B2 | 11/2005 | Nomura | 436/169 |
| 6,968,375 | B1 | 11/2005 | Brown | 709/224 |
| 6,969,359 | B2 | 11/2005 | Duchon | 600/583 |
| 6,969,450 | B2 | 11/2005 | Taniike | 204/403.01 |
| 6,969,451 | B2 | 11/2005 | Shin | 204/412 |
| 6,973,706 | B2 | 12/2005 | Say | 29/595 |
| 6,975,893 | B2 | 12/2005 | Say | 600/347 |
| 6,977,032 | B2 | 12/2005 | Hasegawa | 204/403.05 |
| 6,979,544 | B2 | 12/2005 | Keen | 435/6 |
| 6,979,571 | B2 | 12/2005 | Modzelewski | 436/164 |
| 6,982,027 | B2 | 1/2006 | Yagi | 204/403.06 |
| 6,983,176 | B2 | 1/2006 | Gardner | 600/310 |
| 6,983,177 | B2 | 1/2006 | Rule | 600/310 |
| 6,984,307 | B2 | 1/2006 | Zweig | 205/777.5 |
| 6,986,777 | B2 | 1/2006 | Kim | 606/182 |
| 6,986,869 | B2 | 1/2006 | Tuohy | 422/56 |
| 6,988,996 | B2 | 1/2006 | Roe | 600/584 |
| 6,989,243 | B2 | 1/2006 | Yani | 435/14 |
| 6,989,891 | B2 | 1/2006 | Braig | 356/39 |
| 6,990,365 | B1 | 1/2006 | Parker | 600/328 |
| 6,990,366 | B2 | 1/2006 | Say | 600/345 |
| 6,990,367 | B2 | 1/2006 | Kiser | 600/345 |
| 6,990,849 | B2 | 1/2006 | Bohm | 73/53.01 |
| 6,991,918 | B2 | 1/2006 | Keith | 435/31 |
| 6,991,940 | B2 | 1/2006 | Carroll | 436/514 |
| 6,994,825 | B2 | 2/2006 | Haviland | 422/58 |
| 6,997,317 | B2 | 2/2006 | Catelli | 206/438 |
| 6,997,343 | B2 | 2/2006 | May | 221/232 |
| 6,997,344 | B2 | 2/2006 | Brown | 221/258 |
| 6,997,936 | B2 | 2/2006 | Marshall | 606/181 |
| 6,998,247 | B2 | 2/2006 | Monfre | 435/14 |
| 6,998,248 | B2 | 2/2006 | Yani | 435/14 |

| Patent No. | Date | Name | Class |
|---|---|---|---|
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/309 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/309 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,044,911 B2 | 5/2006 | Drinan | 600/300 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,060,059 B2 | 6/2006 | Keith | 604/504 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Jeong et al. | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorczyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0027328 A1 | 10/2001 | Lum | 606/186 |
| 2001/0031931 A1 | 10/2001 | Cunningham et al. | 600/573 |
| 2001/0054319 A1 | 12/2001 | Heller | 73/849 |
| 2002/0002344 A1 | 1/2002 | Douglas et al. | 600/583 |
| 2002/0004196 A1 | 1/2002 | Whitson | 435/4 |
| 2002/0016606 A1 | 2/2002 | Moerman | 606/181 |

| Publication No. | Date | Name | Class |
|---|---|---|---|
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0044890 A1 | 4/2002 | Black | 422/56 |
| 2002/0052618 A1 | 5/2002 | Haar et al. | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park et al. | 604/21 |
| 2002/0084196 A1 | 7/2002 | Liamos | 205/792 |
| 2002/0087056 A1 | 7/2002 | Aceti | 61/500 |
| 2002/0092612 A1 | 7/2002 | Davies | 156/292 |
| 2002/0103499 A1 | 8/2002 | Perez et al. | 606/182 |
| 2002/0120216 A1 | 8/2002 | Fritz | 600/583 |
| 2002/0120261 A1 | 8/2002 | Morris | 606/41 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | 61/500 |
| 2003/0028126 A1 | 2/2003 | List | 600/583 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 600/576 |
| 2003/0069753 A1 | 4/2003 | Brown | 705/2 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman et al. | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/573 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti | 702/31 |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 60/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0030353 A1 | 2/2004 | Schmelzeisen-R | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0256228 A1 | 2/2004 | Huang | 204/434 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0054898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |

| | | | |
|---|---|---|---|
| 2004/0061841 A1 | 4/2004 Black .................. 355/30 | 2004/0199062 A1 | 10/2004 Petersson ............... 600/316 |
| 2004/0064068 A1 | 4/2004 DeNuzzio ............ 600/583 | 2004/0199409 A1 | 10/2004 Brown .................... 705/3 |
| 2004/0087990 A1 | 5/2004 Boecker ............... 606/181 | 2004/0200720 A1 | 10/2004 Musho ................. 204/403.01 |
| 2004/0092842 A1 | 5/2004 Boecker ............... 600/575 | 2004/0200721 A1 | 10/2004 Bhullar ................ 204/403.01 |
| 2004/0092994 A1 | 5/2004 Briggs ................... 606/181 | 2004/0202576 A1 | 10/2004 Aceti .................... 422/82.05 |
| 2004/0092995 A1 | 5/2004 Boecker ............... 606/181 | 2004/0204662 A1 | 10/2004 Perez .................... 600/583 |
| 2004/0096991 A1 | 5/2004 Zhang ................... 436/518 | 2004/0206625 A1 | 10/2004 Bhullar ................ 204/403.1 |
| 2004/0098009 A1 | 5/2004 Boecker ............... 606/181 | 2004/0206636 A1 | 10/2004 Hodges ................. 205/792 |
| 2004/0098010 A1 | 5/2004 Davison ............... 606/181 | 2004/0206658 A1 | 10/2004 Hammerstedt ........ 206/524.1 |
| 2004/0102803 A1 | 5/2004 Boecker ............... 606/183 | 2004/0209307 A1 | 10/2004 Valkirs .................. 435/7.1 |
| 2004/0106855 A1 | 6/2004 Brown .................. 600/301 | 2004/0209350 A1 | 10/2004 Sakata .................. 435/287.1 |
| 2004/0106858 A1 | 6/2004 Say ...................... 600/345 | 2004/0209354 A1 | 10/2004 Mathies ................ 435/287.2 |
| 2004/0106859 A1 | 6/2004 Say ...................... 600/345 | 2004/0210279 A1 | 10/2004 Gruzdev ................ 607/89 |
| 2004/0106860 A1 | 6/2004 Say ...................... 600/345 | 2004/0211666 A1 | 10/2004 Pamidi ................. 204/403.01 |
| 2004/0106904 A1 | 6/2004 Gonnelli ............... 604/173 | 2004/0214253 A1 | 10/2004 Paek ..................... 435/7.92 |
| 2004/0106941 A1 | 6/2004 Roe ...................... 606/181 | 2004/0215224 A1 | 10/2004 Sakata .................. 606/181 |
| 2004/0107116 A1 | 6/2004 Brown .................. 705/2 | 2004/0215225 A1 | 10/2004 Nakayama ............ 606/182 |
| 2004/0115754 A1 | 6/2004 Chang .................. 435/14 | 2004/0216516 A1 | 11/2004 Sato ...................... 73/64.56 |
| 2004/0116780 A1 | 6/2004 Brown .................. 600/300 | 2004/0217019 A1 | 11/2004 Cai ....................... 205/792 |
| 2004/0116829 A1 | 6/2004 Raney .................. 600/573 | 2004/0219500 A1 | 11/2004 Brown .................. 434/307 R |
| 2004/0117207 A1 | 6/2004 Brown .................. 705/2 | 2004/0219535 A1 | 11/2004 Bell ...................... 435/6 |
| 2004/0117208 A1 | 6/2004 Brown .................. 705/2 | 2004/0220456 A1 | 11/2004 Eppstein ............... 600/309 |
| 2004/0117209 A1 | 6/2004 Brown .................. 705/2 | 2004/0220495 A1 | 11/2004 Cahir .................... 600/562 |
| 2004/0117210 A1 | 6/2004 Brown .................. 705/2 | 2004/0220564 A1 | 11/2004 Ho ........................ 606/47 |
| 2004/0122339 A1 | 6/2004 Roe ...................... 61/0 | 2004/0220603 A1 | 11/2004 Rutynowski ........... 606/181 |
| 2004/0115831 A1 | 7/2004 Meathrel ............... 436/514 | 2004/0222092 A1 | 11/2004 Musho .................. 204/401 |
| 2004/0127818 A1 | 7/2004 Roe ...................... 600/583 | 2004/0224369 A1 | 11/2004 Cai ....................... 435/7.7 |
| 2004/0127819 A1 | 7/2004 Roe ...................... 600/583 | 2004/0225230 A1 | 11/2004 Liamos ................. 600/583 |
| 2004/0127928 A1 | 7/2004 Whitson ............... 606/181 | 2004/0225311 A1 | 11/2004 Levaughn .............. 606/181 |
| 2004/0127929 A1 | 7/2004 Roe ...................... 606/181 | 2004/0225312 A1 | 11/2004 Orloff ................... 606/182 |
| 2004/0132167 A1 | 7/2004 Rule ..................... 435/287.1 | 2004/0230216 A1 | 11/2004 Levaughn .............. 606/181 |
| 2004/0133125 A1 | 7/2004 Miyashita ............. 600/573 | 2004/0231984 A1 | 11/2004 Imants .................. 204/416 |
| 2004/0133127 A1 | 7/2004 Roe ...................... 600/583 | 2004/0232009 A1 | 11/2004 Okuda .................. 205/789 |
| 2004/0137640 A1 | 7/2004 Hirao ................... 436/514 | 2004/0236250 A1 | 11/2004 Hodges ................. 606/181 |
| 2004/0138541 A1 | 7/2004 Ward .................... 600/345 | 2004/0236251 A1 | 11/2004 Roe ...................... 600/583 |
| 2004/0138588 A1 | 7/2004 Saikley ................. 600/583 | 2004/0236268 A1 | 11/2004 Mitragotri ............. 604/20 |
| 2004/0138688 A1 | 7/2004 Giraud .................. 606/181 | 2004/0236362 A1 | 11/2004 Schraga ................ 606/181 |
| 2004/0146958 A1 | 7/2004 Bae ....................... 435/14 | 2004/0023858 A1 | 12/2004 Forrow .................. 204/403 |
| 2004/0154932 A1 | 8/2004 Deng .................... 205/777.5 | 2004/0238357 A1 | 12/2004 Bhullar ................. 204/400 |
| 2004/0157017 A1 | 8/2004 Mauze .................. 428/35.7 | 2004/0238358 A1 | 12/2004 Forrow .................. 204/403 |
| 2004/0157149 A1 | 8/2004 Hofmann .............. 430/131 | 2004/0238359 A1 | 12/2004 Ikeda .................... 204/403.1 |
| 2004/0157319 A1 | 8/2004 Keen .................... 435/287.2 | 2004/0241746 A1 | 12/2004 Adlassnig ............. 435/7.1 |
| 2004/0157338 A1 | 8/2004 Burke ................... 436/147 | 2004/0242977 A1 | 12/2004 Dosmann .............. 600/315 |
| 2004/0157339 A1 | 8/2004 Burke ................... 436/149 | 2004/0243164 A1 | 12/2004 D'Agostino ........... 606/181 |
| 2004/0158137 A1 | 8/2004 Eppstein ............... 600/347 | 2004/0243165 A1 | 12/2004 Koike ................... 606/181 |
| 2004/0158271 A1 | 8/2004 Hamamoto ........... 606/181 | 2004/0245101 A1 | 12/2004 Willner ................. 204/403 |
| 2004/0161737 A1 | 8/2004 Yang .................... 435/5 | 2004/0248282 A1 | 12/2004 Sobha ................... 435/287.2 |
| 2004/0162473 A1 | 8/2004 Sohrab .................. 600/345 | 2004/0248312 A1 | 12/2004 Vreeke .................. 436/95 |
| 2004/0162474 A1 | 8/2004 Kise ..................... 600/345 | 2004/0249254 A1 | 12/2004 Racchini .............. 600/347 |
| 2004/0162506 A1 | 8/2004 Duchon ................ 600/583 | 2004/0249310 A1 | 12/2004 Shartle ................. 600/583 |
| 2004/0162573 A1 | 8/2004 Keheiri ................. 606/182 | 2004/0249311 A1 | 12/2004 Haar ..................... 600/584 |
| 2004/0167383 A1 | 8/2004 Kim ...................... 600/365 | 2004/0249405 A1 | 12/2004 Watanabe .............. 606/181 |
| 2004/0171057 A1 | 9/2004 Yang .................... 435/6 | 2004/0249406 A1 | 12/2004 Griffin .................. 606/182 |
| 2004/0171968 A1 | 9/2004 Katsuki ................ 600/583 | 2004/0251131 A1 | 12/2004 Ueno .................... 204/403 |
| 2004/0172000 A1 | 9/2004 Roe ...................... 604/361 | 2004/0253634 A1 | 12/2004 Wang .................... 435/7.1 |
| 2004/0173472 A1 | 9/2004 Jung ..................... 205/777.5 | 2004/0254434 A1 | 12/2004 Goodnow .............. 600/365 |
| 2004/0173488 A1 | 9/2004 Griffin .................. 206/363 | 2004/0254599 A1 | 12/2004 Lipoma ................. 606/181 |
| 2004/0176705 A1 | 9/2004 Stevens ................. 600/584 | 2004/0256248 A1 | 12/2004 Burke ................... 205/792 |
| 2004/0176732 A1 | 9/2004 Frazier .................. 604/345 | 2004/0256685 A1 | 12/2004 Chou .................... 257/414 |
| 2004/0178066 A1 | 9/2004 Miyazaki .............. 204/403.01 | 2004/0258564 A1 | 12/2004 Charlton ............... 422/58 |
| 2004/0178067 A1 | 9/2004 Miyazaki .............. 204/403.1 | 2004/0260204 A1 | 12/2004 Boecker ................ 600/584 |
| 2004/0178216 A1 | 9/2004 Brickwood ........... 221/268 | 2004/0260324 A1 | 12/2004 Fukuzawa ............. 606/181 |
| 2004/0180379 A1 | 9/2004 van Duyane .......... 435/7.1 | 2004/0260325 A1 | 12/2004 Kuhr ..................... 606/181 |
| 2004/0182703 A1 | 9/2004 Bell ...................... 204/403.11 | 2004/0260326 A1 | 12/2004 Lipoma ................. 606/182 |
| 2004/0185568 A1 | 9/2004 Matsumoto ........... 436/8 | 2004/0260511 A1 | 12/2004 Burke ................... 702/182 |
| 2004/0186359 A1 | 9/2004 Beaudoin .............. 600/310 | 2004/0267105 A1 | 12/2004 Monfre ................. 600/344 |
| 2004/0186394 A1 | 9/2004 Rose ..................... 600/598 | 2004/0267160 A9 | 12/2004 Perez .................... 600/583 |
| 2004/0186500 A1 | 9/2004 Koilke .................. 606/181 | 2004/0267229 A1 | 12/2004 Moerman .............. 604/500 |
| 2004/0193201 A1 | 9/2004 Kim ...................... 606/181 | 2004/0267299 A1 | 12/2004 Kuriger ................. 606/181 |
| 2004/0193377 A1 | 9/2004 Brown .................. 702/19 | 2004/0267300 A1 | 12/2004 Mace .................... 606/182 |
| 2004/0194302 A1 | 10/2004 Bhullar ................ 29/847 | 2005/0000806 A1 | 1/2005 Hsieh .................... 203/403.1 |
| 2004/0197231 A1 | 10/2004 Katsuki ................ 422/68.1 | 2005/0000807 A1 | 1/2005 Wang .................... 204/403.81 |
| 2004/0197821 A1 | 10/2004 Bauer ................... 437/7.1 | 2005/0000808 A1 | 1/2005 Cui ....................... 203/403.14 |

| Pub. No. | Date | Name | Class |
|---|---|---|---|
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Rutchi | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027211 A1 | 2/2005 | Kuhr | 600/583 |
| 2005/0027562 A1 | 2/2005 | Brown | 705/2 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Katsuji | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049473 A1 | 3/2005 | Desai et al. | 600/347 |
| 2005/0050859 A1 | 3/2005 | Coppeta | 53/471 |
| 2005/0054082 A1 | 3/2005 | Pachl | 435/287.2 |
| 2005/0059895 A1 | 3/2005 | Brown | 600/481 |
| 2005/0060194 A1 | 3/2005 | Brown | 705/2 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077587 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/181 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/356 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/143 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Salto | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Huber | 600/322 |

| Pub. No. | Date | Name | Class |
|---|---|---|---|
| 2005/0192488 A1 | 9/2005 | Brynton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0204778 A1 | 10/2005 | Saito | 713/176 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Day | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030788 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052724 A1 | 3/2006 | Roe | 600/583 |
| 2006/0052733 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chaung | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |
| 2006/0096859 A1 | 5/2006 | King Tong Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crosman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |

| | | | | |
|---|---|---|---|---|
| 2006/0155215 A1 | 7/2006 | Cha | | 600/583 |
| 2006/0155316 A1 | 7/2006 | Perez | | 606/181 |
| 2006/0155317 A1 | 7/2006 | List | | 606/181 |
| 2006/0156796 A1 | 7/2006 | Burke | | 73/61.44 |
| 2006/0157362 A1 | 7/2006 | Schraga | | 206/363 |
| 2006/0161078 A1 | 7/2006 | Schraga | | 600/583 |
| 2006/0161194 A1 | 7/2006 | Freeman | | 606/185 |
| 2006/0166302 A1 | 7/2006 | Clarke | | 435/25 |
| 2006/0167382 A1 | 7/2006 | Deshmukh | | 600/583 |
| 2006/1051342 | 7/2006 | Yaguchi | | 206/306 |
| 2006/0169599 A1 | 8/2006 | Feldman | | 205/792 |
| 2006/0173254 A1 | 8/2006 | Acosta | | 600/316 |
| 2006/0173255 A1 | 8/2006 | Acosta | | 600/316 |
| 2006/0173379 A1 | 8/2006 | Rasch-Menges | | 600/583 |
| 2006/0173380 A1 | 8/2006 | Hoenes | | 600/583 |
| 2006/0173478 A1 | 8/2006 | Schraga | | 606/181 |
| 2006/0175216 A1 | 8/2006 | Freeman | | 206/363 |
| 2006/0178573 A1 | 8/2006 | Kermani | | 600/347 |
| 2006/0178599 A1 | 8/2006 | Faupel | | 600/578 |
| 2006/0178600 A1 | 8/2006 | Kennedy | | 600/584 |
| 2006/0178686 A1 | 8/2006 | Schraga | | 606/181 |
| 2006/0178687 A1 | 8/2006 | Freeman | | 606/181 |
| 2006/0178688 A1 | 8/2006 | Freeman | | 606/181 |
| 2006/0178689 A1 | 8/2006 | Freeman | | 606/181 |
| 2006/0178690 A1 | 8/2006 | Freeman | | 606/181 |
| 2006/0183871 A1 | 8/2006 | Ward | | 525/464 |
| 2006/0183983 A1 | 8/2006 | Acosta | | 600/316 |
| 2006/0184101 A1 | 8/2006 | Srinivasan | | 604/68 |
| 2006/0188395 A1 | 8/2006 | Taniike | | 422/57 |
| 2006/0189584 A1 | 8/2006 | Neel | | 600/584 |
| 2006/0191787 A1 | 8/2006 | Wang | | 204/400 |
| 2006/0195023 A1 | 8/2006 | Acosta | | 600/316 |
| 2006/0195047 A1 | 8/2006 | Freeman | | 600/583 |
| 2006/0195128 A1 | 8/2006 | Alden | | 606/181 |
| 2006/0195129 A1 | 8/2006 | Freeman | | 606/181 |
| 2006/0195130 A1 | 8/2006 | Freeman | | 606/181 |
| 2006/0195131 A1 | 8/2006 | Freeman | | 606/181 |
| 2006/0195132 A1 | 8/2006 | Freeman | | 606/181 |
| 2006/0195133 A1 | 8/2006 | Freeman | | 606/181 |
| 2006/0196031 A1 | 9/2006 | Hoenes | | 29/432 |
| 2006/0196795 A1 | 9/2006 | Windus-Smith | | 206/438 |
| 2006/0200044 A1 | 9/2006 | Freeman | | 600/583 |
| 2006/0200045 A1 | 9/2006 | Roe | | 600/583 |
| 2006/0200046 A1 | 9/2006 | Windus-Smith | | 600/583 |
| 2006/0200181 A1 | 9/2006 | Fukuzawa | | 606/181 |
| 2006/0200981 A1 | 9/2006 | Bhullar | | 29/847 |
| 2006/0200982 A1 | 9/2006 | Bhullar | | 29/847 |
| 2006/0204399 A1 | 9/2006 | Freeman | | 422/58 |
| 2006/0205029 A1 | 9/2006 | Heller | | 435/25 |
| 2006/0205060 A1 | 9/2006 | Kim | | 435/287.2 |
| 2006/0206135 A1 | 9/2006 | Uehata | | 606/181 |
| 2006/0211127 A1 | 9/2006 | Iwaki | | 436/169 |
| 2006/0211927 A1 | 9/2006 | Acosta | | 600/316 |
| 2006/0211931 A1 | 9/2006 | Blank | | 600/344 |
| 2006/0219551 A1 | 10/2006 | Edelbrock | | 204/403.14 |
| 2006/0222567 A1 | 10/2006 | Kloepfer | | 422/68.1 |
| 2006/0224171 A1 | 10/2006 | Sakata | | 606/181 |
| 2006/0224172 A1 | 10/2006 | Lavaughn | | 606/181 |
| 2006/0229532 A1 | 10/2006 | Wong | | 600/583 |
| 2006/0229533 A1 | 10/2006 | Hoenes | | 600/584 |
| 2006/0229651 A1 | 10/2006 | Marshall | | 606/181 |
| 2006/0231396 A1 | 10/2006 | Yamaoka | | 204/403.14 |
| 2006/0231418 A1 | 10/2006 | Harding | | 205/775 |
| 2006/0231442 A1 | 10/2006 | Windus-Smith | | 206/438 |
| 2006/0234369 A1 | 10/2006 | Sih | | 435/287.1 |
| 2006/0235284 A1 | 10/2006 | Lee | | 600/345 |
| 2006/0235454 A1 | 10/2006 | LeVaughn | | 606/181 |
| 2006/0241517 A1 | 10/2006 | Fowler | | 600/583 |
| 2006/0241666 A1 | 10/2006 | Briggs | | 606/181 |
| 2006/0241667 A1 | 10/2006 | Freeman | | 606/181 |
| 2006/0241668 A1 | 10/2006 | Schraga | | 606/181 |
| 2006/0241669 A1 | 10/2006 | Stout | | 606/182 |
| 2006/0247554 A1 | 11/2006 | Rose | | 600/583 |
| 2006/0247555 A1 | 11/2006 | Harttig | | 600/584 |
| 2006/0247670 A1 | 11/2006 | LeVaughn | | 606/181 |
| 2006/0247671 A1 | 11/2006 | Levaughn | | 606/182 |
| 2006/0259057 A1 | 11/2006 | Kim | | 606/181 |
| 2006/0259058 A1 | 11/2006 | Schiff | | 606/181 |
| 2006/0259060 A1 | 11/2006 | Whitson | | 606/182 |
| 2006/0264718 A1 | 11/2006 | Ruchti | | 600/310 |
| 2006/0264996 A1 | 11/2006 | Levaughn | | 606/181 |
| 2006/0264997 A1 | 11/2006 | Colonna | | 606/181 |
| 2006/0271083 A1 | 11/2006 | Boecker | | 606/181 |
| 2006/0271084 A1 | 11/2006 | Schraga | | 606/182 |
| 2006/0276724 A1 | 12/2006 | Freeman | | 600/583 |
| 2006/0277048 A1 | 12/2006 | Kintzig | | 704/275 |
| 2006/0278545 A1 | 12/2006 | Henning | | 206/363 |
| 2006/0282109 A1 | 12/2006 | Jansen | | 606/181 |
| 2006/0286620 A1 | 12/2006 | Werner | | 435/14 |
| 2006/0287664 A1 | 12/2006 | Grage | | 606/181 |
| 2006/0293577 A1 | 12/2006 | Morrison | | 600/365 |
| 2007/0004989 A1 | 1/2007 | Dhillon | | 600/583 |
| 2007/0004990 A1 | 1/2007 | Kistner | | 600/583 |
| 2007/0007183 A1 | 1/2007 | Schulat | | 209/573 |
| 2007/0009381 A1 | 1/2007 | Schulat | | 422/58 |
| 2007/0010839 A1 | 1/2007 | Galloway | | 606/167 |
| 2007/0010841 A1 | 1/2007 | Teo | | 606/181 |
| 2007/0015978 A1 | 1/2007 | Kanayama | | 600/310 |
| 2007/0016079 A1 | 1/2007 | Freeman | | 600/476 |
| 2007/0016103 A1 | 1/2007 | Calasso | | 600/583 |
| 2007/0016104 A1 | 1/2007 | Jansen | | 600/583 |

FOREIGN PATENT DOCUMENTS

| | | |
|---|---|---|
| DE | 29824204 | 10/2000 |
| DE | 10032042 | 1/2002 |
| DE | 10057832 | 2/2002 |
| DE | 10057832 C1 | 2/2002 |
| DE | 10142232 | 3/2003 |
| DE | 10208575 C1 | 8/2003 |
| DE | 10245721 | 12/2003 |
| DE | 10361560 A1 | 7/2005 |
| EP | 0289 269 | 11/1988 |
| EP | 0320109 | 6/1989 |
| EP | 0170375 | 5/1990 |
| EP | 0136362 | 12/1990 |
| EP | 0453283 | 10/1991 |
| EP | 0263948 | 2/1992 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |
| EP | 0359831 | 9/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0560336 | 5/1998 |
| EP | 0560336 | 6/1998 |
| EP | 0878 708 | 11/1998 |
| EP | 0505475 | 3/1999 |
| EP | 0901018 | 3/1999 |
| EP | 0470649 | 6/1999 |
| EP | 0847447 | 11/1999 |
| EP | 0964059 | 12/1999 |
| EP | 0969097 | 1/2000 |

| | | | | | | |
|---|---|---|---|---|---|---|
| EP | 1021950 | 7/2000 | | WO | WO 00/18293 | 4/2000 |
| EP | 0894869 | 2/2001 | | WO | WO 00/19346 | 4/2000 |
| EP | 1074832 | 2/2001 | | WO | WO 00/30186 | 5/2000 |
| EP | 1093854 | 4/2001 | | WO | WO 00/32097 | 6/2000 |
| EP | 1 101 443 A2 | 5/2001 | | WO | WO 00/33236 | 6/2000 |
| EP | 114995 | 7/2001 | | WO | WO 003/32098 | 6/2000 |
| EP | 1114995 | 7/2001 | | WO | WO 00/39914 | 7/2000 |
| EP | 0736607 | 8/2001 | | WO | WO 00/44084 | 7/2000 |
| EP | 0874984 | 11/2001 | | WO | WO 0039914 | 7/2000 |
| EP | 0730037 | 12/2001 | | WO | WO 0042422 | 7/2000 |
| EP | 0636879 | 1/2002 | | WO | WO 00/50771 | 8/2000 |
| EP | 01174083 | 1/2002 | | WO | WO 00/60340 | 10/2000 |
| EP | 0851224 | 3/2002 | | WO | WO 00/64022 | 10/2000 |
| EP | 0759553 | 5/2002 | | WO | WO 00/37245 | 11/2000 |
| EP | 0856586 | 5/2002 | | WO | WO 00/67245 | 11/2000 |
| EP | 0817809 | 7/2002 | | WO | WO 00/67268 | 11/2000 |
| EP | 0872728 | 7/2002 | | WO | WO 00/72452 | 11/2000 |
| EP | 0795748 | 8/2002 | | WO | WO 00/00090 | 1/2001 |
| EP | 0685737 | 9/2002 | | WO | WO 01/00090 | 1/2001 |
| EP | 0958495 | 11/2002 | | WO | WO 01/00090 A1 | 1/2001 |
| EP | 0937249 | 12/2002 | | WO | WO 01/75433 | 3/2001 |
| EP | 0880692 | 1/2004 | | WO | WO 01/23885 | 4/2001 |
| EP | 01374770 | 1/2004 | | WO | WO 01/25775 | 4/2001 |
| EP | 1246688 | 5/2004 | | WO | WO 01/26813 | 4/2001 |
| EP | 1502614 | 2/2005 | | WO | WO 01/33216 | 5/2001 |
| GB | 2168815 | 6/1986 | | WO | WO 01/34029 | 5/2001 |
| GB | 2 335 990 A | 10/1999 | | WO | WO 01/36955 | 5/2001 |
| JP | 2-326247 | 11/1990 | | WO | WO 01/37174 | 5/2001 |
| JP | 10-296325 | 10/1998 | | WO | WO 01/40788 | 7/2001 |
| WO | WO 1980/01389 | 7/1980 | | WO | WO 01/57510 | 8/2001 |
| WO | WO 1985/04089 | 9/1985 | | WO | WO 01/64105 | 9/2001 |
| WO | WO 1986/07632 | 12/1985 | | WO | WO 01/66010 | 9/2001 |
| WO | WO 1991/09139 | 6/1991 | | WO | WO 01/66010 A1 | 9/2001 |
| WO | WO 1993/06979 | 4/1993 | | WO | WO 01/69505 | 9/2001 |
| WO | WO 1993/25898 | 12/1993 | | WO | WO 01/72225 | 10/2001 |
| WO | WO 1994/27140 | 11/1994 | | WO | WO 01/73124 | 10/2001 |
| WO | WO 1994/29703 | 12/1994 | | WO | WO 01/73395 | 10/2001 |
| WO | WO 1994/29704 | 12/1994 | | WO | WO 01/89691 | 11/2001 |
| WO | WO 1994/29731 | 12/1994 | | WO | WO 02/00101 | 1/2002 |
| WO | WO 1995/00662 | 1/1995 | | WO | WO 02/02796 | 1/2002 |
| WO | WO 1995/10223 | 4/1995 | | WO | WO 02/08750 | 1/2002 |
| WO | WO 1995/22597 | 8/1995 | | WO | WO 02/08753 | 1/2002 |
| WO | WO 1996/30431 | 10/1996 | | WO | WO 02/08950 | 1/2002 |
| WO | WO 1997/02359 | 1/1997 | | WO | WO 02/18940 | 3/2002 |
| WO | WO 1997/02487 | 1/1997 | | WO | WO 02/21317 | 3/2002 |
| WO | WO 1997/18317 | 5/1997 | | WO | WO 02/32559 | 4/2002 |
| WO | WO 1997/30344 | 8/1997 | | WO | WO 02/25551 | 5/2002 |
| WO | WO97/42888 | 11/1997 | | WO | WO 02/41227 | 5/2002 |
| WO | WO 1997/42882 | 11/1997 | | WO | WO 02/41779 | 5/2002 |
| WO | WO 1997/45720 | 12/1997 | | WO | WO 02/44948 | 6/2002 |
| WO | WO 1998/03431 | 1/1998 | | WO | WO 02/056769 A1 | 7/2002 |
| WO | WO 1998/19159 | 5/1998 | | WO | WO 02/059734 | 8/2002 |
| WO | WO 1998/20332 | 5/1998 | | WO | WO 02/069791 | 9/2002 |
| WO | WO 1998/20348 | 5/1998 | | WO | WO 02/077638 | 10/2002 |
| WO | WO 1998/24366 | 6/1998 | | WO | WO 02/100251 | 12/2002 |
| WO | WO 1998/35225 | 8/1998 | | WO | WO 02/100252 | 12/2002 |
| WO | WO 1999/03584 | 1/1999 | | WO | WO 02/100253 | 12/2002 |
| WO | WO 1999/05966 | 2/1999 | | WO | WO 02/100254 | 12/2002 |
| WO | WO 1999/13100 | 3/1999 | | WO | WO 02/100460 | 12/2002 |
| WO | WO 99/17854 | 4/1999 | | WO | WO 02/100461 | 12/2002 |
| WO | WO 99/18532 | 4/1999 | | WO | WO 02/101343 | 12/2002 |
| WO | WO 1999/19507 | 4/1999 | | WO | WO 02/101359 | 12/2002 |
| WO | WO 1999/19717 | 4/1999 | | WO | WO 03/000321 | 1/2003 |
| WO | WO 99/27483 | 6/1999 | | WO | WO 03/023389 | 3/2003 |
| WO | WO 1999/27852 | 6/1999 | | WO | WO 03/042691 | 5/2003 |
| WO | WO 1999/62576 | 12/1999 | | WO | WO 03/045557 | 6/2003 |
| WO | WO 1999/64580 | 12/1999 | | WO | WO 03/046542 | 6/2003 |
| WO | WO 00/06024 | 2/2000 | | WO | WO 03/049609 | 6/2003 |
| WO | WO 00/09184 | 2/2000 | | WO | WO 03/050534 | 6/2003 |
| WO | WO 00/11578 | 3/2000 | | WO | WO 03/066128 | 8/2003 |
| WO | WO 00/15103 | 3/2000 | | WO | WO 03/070099 | 8/2003 |
| WO | WO 00/17799 | 3/2000 | | WO | WO 03/071940 | 9/2003 |
| WO | WO 00/17800 | 3/2000 | | WO | WO 2003/094752 | 11/2003 |

| | | | | | | |
|---|---|---|---|---|---|---|
| WO | WO 03/101297 | 12/2003 | | WO | WO 2005/018710 | 3/2005 |
| WO | WO 04/008130 | 1/2004 | | WO | WO 2005/018711 | 3/2005 |
| WO | WO 2004022133 | 3/2004 | | WO | WO 2005/023088 | 3/2005 |
| WO | WO 04/026130 | 4/2004 | | WO | WO 2005/033659 | 4/2005 |
| WO | WO 04/040285 | 5/2004 | | WO | WO 2005/034720 | 4/2005 |
| WO | WO 04/040287 A1 | 5/2004 | | WO | WO 2005/034721 | 4/2005 |
| WO | WO 04/040948 | 5/2004 | | WO | WO 2005/034741 | 4/2005 |
| WO | WO 04/041082 | 5/2004 | | WO | WO 2005/034778 | 4/2005 |
| WO | WO 04/054455 | 7/2004 | | WO | WO 2005/035017 | 4/2005 |
| WO | WO 04/060174 | 7/2004 | | WO | WO 2005/035018 | 4/2005 |
| WO | WO 04/060446 | 7/2004 | | WO | WO 2005/037095 | 4/2005 |
| WO | WO 04/091693 | 10/2004 | | WO | WO 2005/046477 | 5/2005 |
| WO | WO 04/098405 | 11/2004 | | WO | WO 2005/065399 | 7/2005 |
| WO | WO 04/107964 | 12/2004 | | WO | WO 2005/065414 | 7/2005 |
| WO | WO 04/107975 | 12/2004 | | WO | WO 2005/065415 | 7/2005 |
| WO | WO 04/112602 | 12/2004 | | WO | WO 065545 A2 | 7/2005 |
| WO | WO 2004/003147 | 12/2004 | | WO | WO 05/072604 | 8/2005 |
| WO | WO 2004/107964 | 12/2004 | | WO | WO 2005/084557 | 9/2005 |
| WO | WO 04107975 | 12/2004 | | WO | WO 05/116622 | 12/2005 |
| WO | WO 05/001418 | 1/2005 | | WO | WO 05/119234 | 12/2005 |
| WO | WO 2005/001418 | 1/2005 | | WO | WO 05/121759 | 12/2005 |
| WO | WO 2005/006939 | 1/2005 | | WO | WO 06/001973 | 1/2006 |
| WO | WO 2005/011774 | 2/2005 | | WO | WO 06/011062 | 2/2006 |
| WO | WO 2005/016125 | 2/2005 | | WO | WO 06/013045 | 2/2006 |
| WO | WO 05/022143 | 3/2005 | | WO | WO 06/027702 A2 | 3/2006 |
| WO | WO 2005/018425 | 3/2005 | | WO | WO 06032391 | 3/2006 |
| WO | WO 2005/018430 | 3/2005 | | WO | WO 2006/072004 | 7/2006 |
| WO | WO 2005/018454 | 3/2005 | | | | |
| WO | WO 2005/018709 | 3/2005 | | | | |

* cited by examiner

SELF OPTIMIZING LANCING DEVICE WITH ADAPTATION MEANS TO TEMPORAL VARIATIONS IN CUTANEOUS PROPERTIES

TECHNICAL FIELD

Lancing devices are well known in the medical health-care products industry for piercing the skin to produce blood for analysis. Biochemical analysis of blood samples is a diagnostic tool for determining clinical information. Many point-of-care tests are performed using capillary whole blood, the most common being monitoring diabetic blood glucose level. Other uses for this method include the analysis of coagulation based on Prothrombin time measurement. Typically, a drop of blood for this type of analysis is obtained by making a small incision in the fingertip, creating a small wound, which generates a small blood droplet on the surface of the skin.

BACKGROUND ART

Early methods of lancing included piercing or slicing the skin with a needle or razor. Current methods utilize lancet drivers that contain a multitude of spring, cam and mass actuators to drive the lancet. These include cantilever springs, diaphragms, coil springs, as well as gravity plumbs used to actuate the lancet. Typically, the device is pre-cocked, or the user cocks the device. The device is held against the skin and the user, or pressure from the users skin, mechanically triggers the ballistic launch of the lancet. The forward movement, and depth of skin penetration of the lancet is determined by a mechanical stop and/or damping, as well as a spring or cam which retract the lancet.

Current devices generally rely on adjustable mechanical stops or damping to control the lancet's depth of penetration to compensate for skin thickness and hydration. Such devices have the possibility of multiple strikes due to recoil, in addition to vibratory stimulation of the severed nerves as the driver impacts the end of the launcher stop. Cams may offer rough control of lancet velocity in and out of the skin, but do not allow for compensation for skin thickness and hydration. Variations in skin thickness and hydration may yield different results in terms of pain perception, blood yield and success of obtaining blood from different users of the lancing device.

DISCLOSURE OF INVENTION

Embodiments of the present invention are related to medical health-care products and to methods for obtaining body fluids for chemical analysis. More particularly, embodiments of the invention relate to devices and methods for piercing the skin (lancing) using an electrically driven lancet having user definable lancet parameters such as lancet displacement, velocity of incision, retraction, acceleration, and tissue dwell time. A device having features of the invention can compensate for long-term changes in skin physiology, nerve function, and peripheral vascular perfusion such as occurs in diabetes, as well as diurnal variation in skin tensile properties. Alternatively, a device having features of the invention can compensate for skin differences between widely differing populations such as pediatric and geriatric patients.

An embodiment of the invention is directed to a lancing device which controls the advancement and retraction of a lancet by monitoring the position of the lancet in conjunction with a control feedback for modulating the lancet driver to follow a predetermined profile.

BRIEF DESCRIPTION OF DRAWING

The objects, advantages and features of this invention will be more readily appreciated from the following detailed description, when read in conjunction with the accompanying drawing, in which.

BEST MODE FOR CARRYING OUT THE INVENTION

Figure 1A:
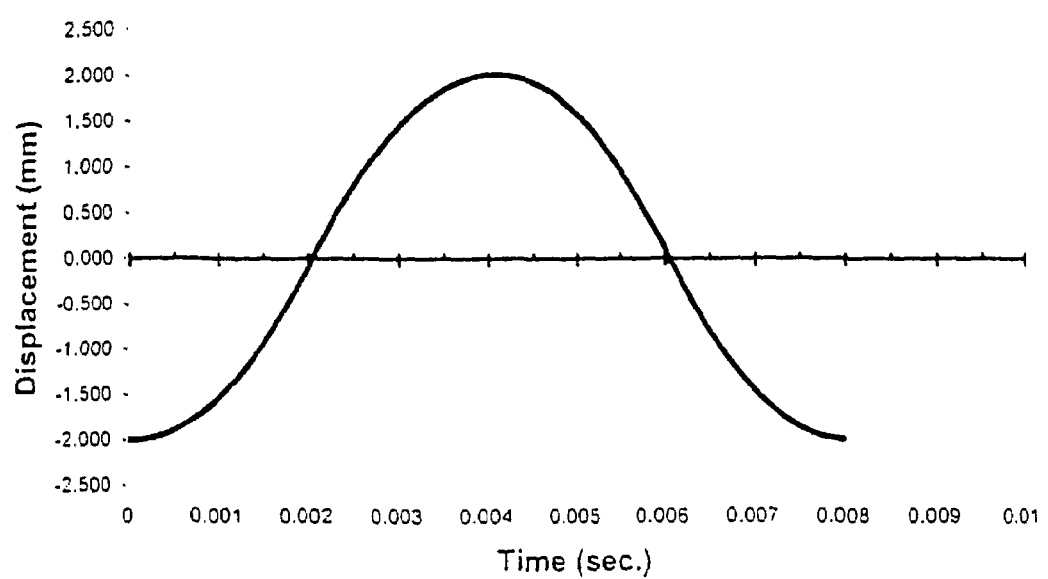
FIGS. 1A and 2A illustrate the displacement over time profile of a harmonic spring/mass system and a controlled lancet.

Lancing device is generally defined to mean any self-contained device for puncturing the skin for the purpose of obtaining a body fluid sample. Lancing devices are typically disposable and reusable in their entirety, or in part. For example, some lancing devices are disposed of as biohaz-ards after one usage. Other lancing devices dispose of only the portions that come in contact with the skin.

Lancet is generally defined to mean any sharp or blunt member used to puncture the skin for the purpose of cutting blood vessels and allowing blood to flow to the surface of the skin. The lancet has certain parameters such as diameter to define the cross-sectional area of the member, and geometry to define the shape of the distal or front lancing end of the member.

Lancet driver is generally defined to mean any means for controlling the advancement and retraction of the lancet Examples of lancet drivers can include spring-actuated drivers, electromagnetic drivers and piezoelectric drivers. Examples of electromagnetic drivers include solenoids, linear induction motors, and linear reluctance motors.

Feedback loop is generally defined to mean a feedback control loop where information is collected about the current behavior of the lancet (such as relative lancet position, rate and direction of lancet motion, resistance to lancet motion, etc.) and is used to modulate the drive power applied to the lancet.

Processor is generally defined to mean a high-speed digital processor containing memory and calculation capabilities. Such processor is used to modulate the lancet driver. Modulate is generally defined to mean controlling the profile of the lancet.

Profile is generally defined to mean a displacement, velocity or acceleration versus time plot or table.

Typically, the lancet and the lancet driver are configured so that lancet velocity is high at the moment of first contact with the skin, decelerates to zero at the predetermined penetration depth, and immediately retracts from the skin, leaving at approximately the same velocity that it entered. The energy required for lancet actuation is initially stored as potential energy, as in the actuators discussed above. During the lancing cycle, the stored energy is transferred into the kinetic energy of the lancet, which is then transferred to potential energy at the apex of the trajectory, and is immediately transferred back into kinetic energy by the retraction mechanism. The actuation and retraction velocities are similar, though opposite in sign. The devices which employ spring or cam driving methods have a symmetrical actuation displacement and velocity profile on the advancement and retraction of the lancet. In most of the available lancet devices, once the launch is initiated, the stored energy determines the velocity profile until the energy is dissipated. Piezoelectric assisted cutting methods have also been described; however, the launching mechanism is spring driven, and no feedback is described for controlling lancet motion. Variations in skin properties require controlling impact, retraction velocity, and dwell time of the lancet within the tissue.

Advantages are achieved by taking into account that tissue dwell time is related to the amount of skin deformation as the lancet tries to puncture the surface of the skin and variance in skin deformation from patient to patient based on skin hydration with regard to dwell time and the necessity to achieve at least 100 microns of skin depth to successfully sample blood.

Pain reduction can be achieved through both the rapid lancet cutting speed and light weight of the proposed lancet. The rapid cutting minimizes the shock waves produced when the lancet strikes the skin in addition to compressing the skin for efficient cutting. Due to the very light mass of the lancet and lack of mechanical stop, there is insubstantial or no vibrational energy transferred to the finger during cutting.

Lancing devices such as the spring and cam driven devices typically yield 70–80% success rate in obtaining a blood droplet, as some lancing events are unsuccessful. Success rate is dependent on reaching the blood capillaries and venuoles, which yield the blood sample. Due to variation in skin thickness and hydration, some skin will deform more before cutting starts, and hence the actual depth of penetration will be less, resulting in less capillaries and venuoles cut. An electronic feedback mechanism yields accurate measurement of skin resistance, and therefore depth of penetration and thus directly improves the success rate of blood yield.

Spontaneous blood yield occurs when blood from the cut vessels flows up the wound tract to the surface of the skin, where it can be collected and tested. Tissue elasticity parameters may force the wound tract to close behind the retracting lancet preventing the blood from reaching the surface. If however, the lancet were to dwell before being retracted, and or be withdrawn slowly from the wound tract, thus keeping the wound open, blood could flow up the patent channel, as described in a copending application Ser. No. 10/363,509, Inventors: Boecker, et al., entitled "METHOD AND APPARATUS FOR IMPROVING SUCCESS RATE OF BLOOD YIELD FROM A FINGERSTICK") submitted on the same day and assigned to the same assignee as the present application. Said copending application is incorporated by reference in its entirety herein.

The ability to control the lancet speed into and out of the wound is critical as it allows the device to compensate for changes in skin thickness and variations in skin hydration to achieve spontaneous blood yield with maximum success rate while minimizing pain. This is done by taking into consideration the skin deformation to achieve a desirable tissue dwell time and depth of penetration.

Figure 1B:
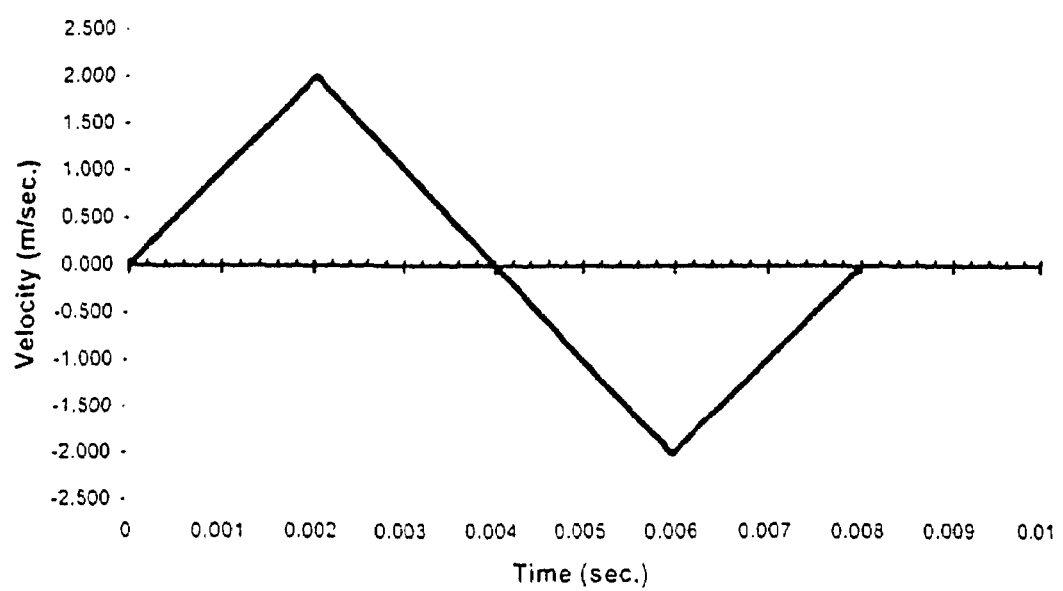
FIGS. 1B and 2B illustrate the velocity over time profiles of a harmonic spring/mass system and a controlled lancet.
Figure 2A:
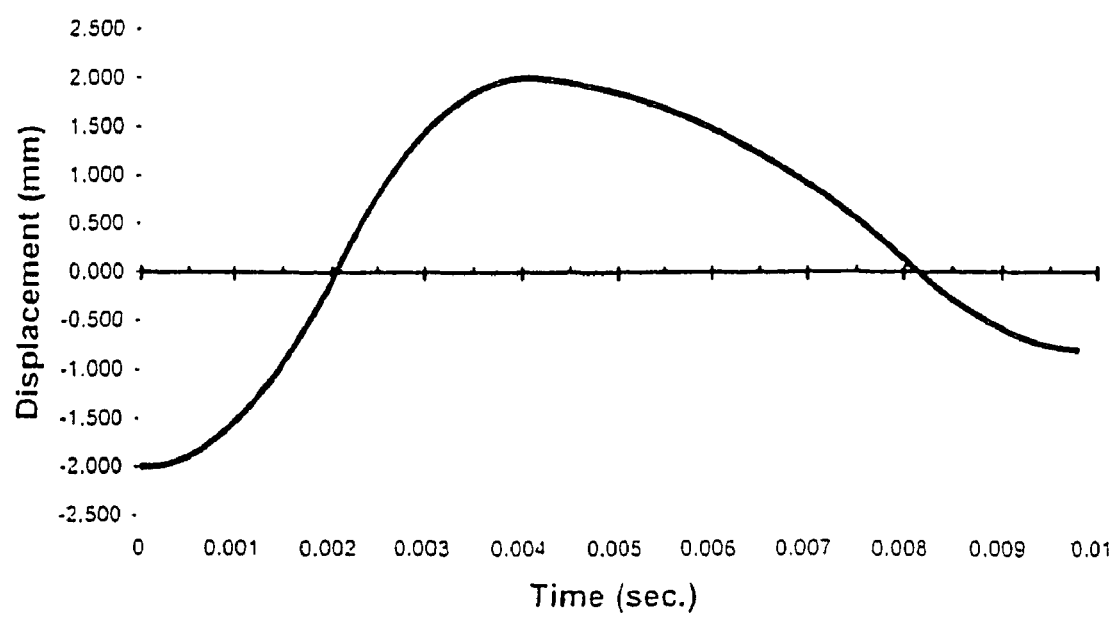
Figure 2B:
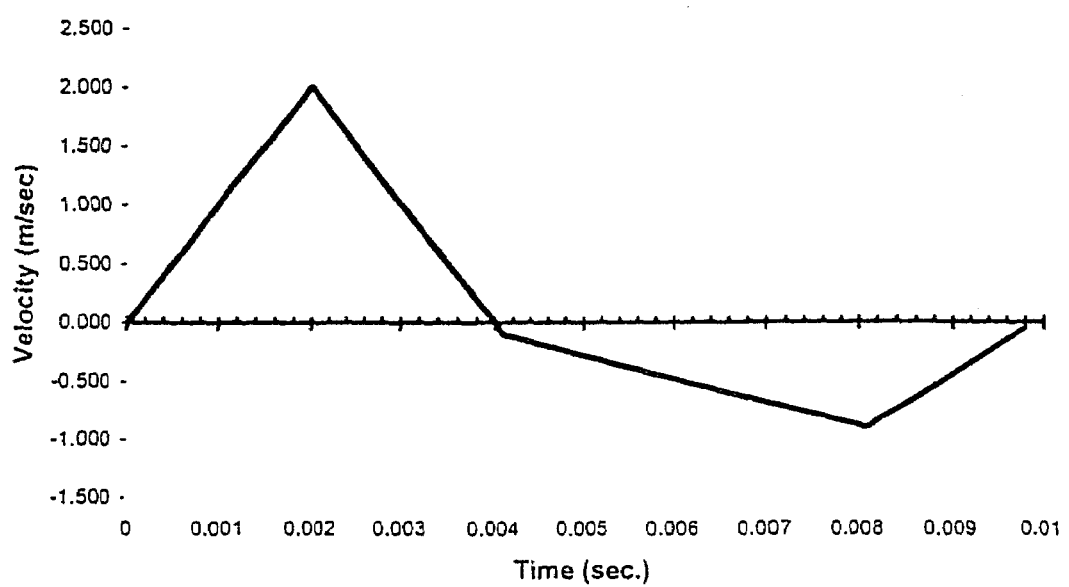

This ability to control velocity and depth of penetration therefore requires an actuation mechanism where feedback is an integral part of driver control. An example of such a driver is the electromagnetic actuator design as described in a copending application Ser. No. 60/298,055, Inventors: Don Alden, et al., entitled "ELECTRIC LANCET ACTUATOR") submitted on the same day and assigned to the same assignee as the present application. Said copending application is incorporated by reference in its entirety herein. Such drivers can control either metal or polymeric lancets. The dynamic control of such a driver is shown in FIG. 2A which illustrates the controlled displacement profile and FIG. 2B which illustrates the controlled velocity profile. These are compared to FIGS. 1A and 1B which illustrate the displacement and velocity profiles, respectively, of a harmonic spring/mass system.

It is, accordingly, an advantage to control the lancet displacement, velocity, and acceleration at several steps in the lancing cycle. Such control increases the success rate of obtaining an acceptable sample volume of blood and the ability to obtain a spontaneous blood sample, and decreases the pain perceived by the patient during the lancing procedure. Reduced pain is achieved because of fast entry of the lancet into the tissue. Reduced lancet velocity with increased lancet dwell time in the tissue at a point where the lancet intersects the venuoles and capillary mesh, allows the blood to pool, promoting uninhibited flow into the exit channel. Retraction of the lancet at a low velocity following the sectioning of the venuole/capillary mesh allows the blood to flood the wound tract and flow freely to the surface, thus using the lancet to keep the channel open during retraction. Low-velocity retraction of the lancet near the wound flap prevents the wound flap from sealing off the channel. Thus, the ability to slow the lancet retraction directly contributes to increasing the success rate of obtaining blood. Increasing the sampling success rate to near 100% is considered an essential prerequisite to combine sampling and acquisition into an integrated sampling module (e.g. an integrated glucose sampling module which incorporates a glucose test strip).

Figure 3:
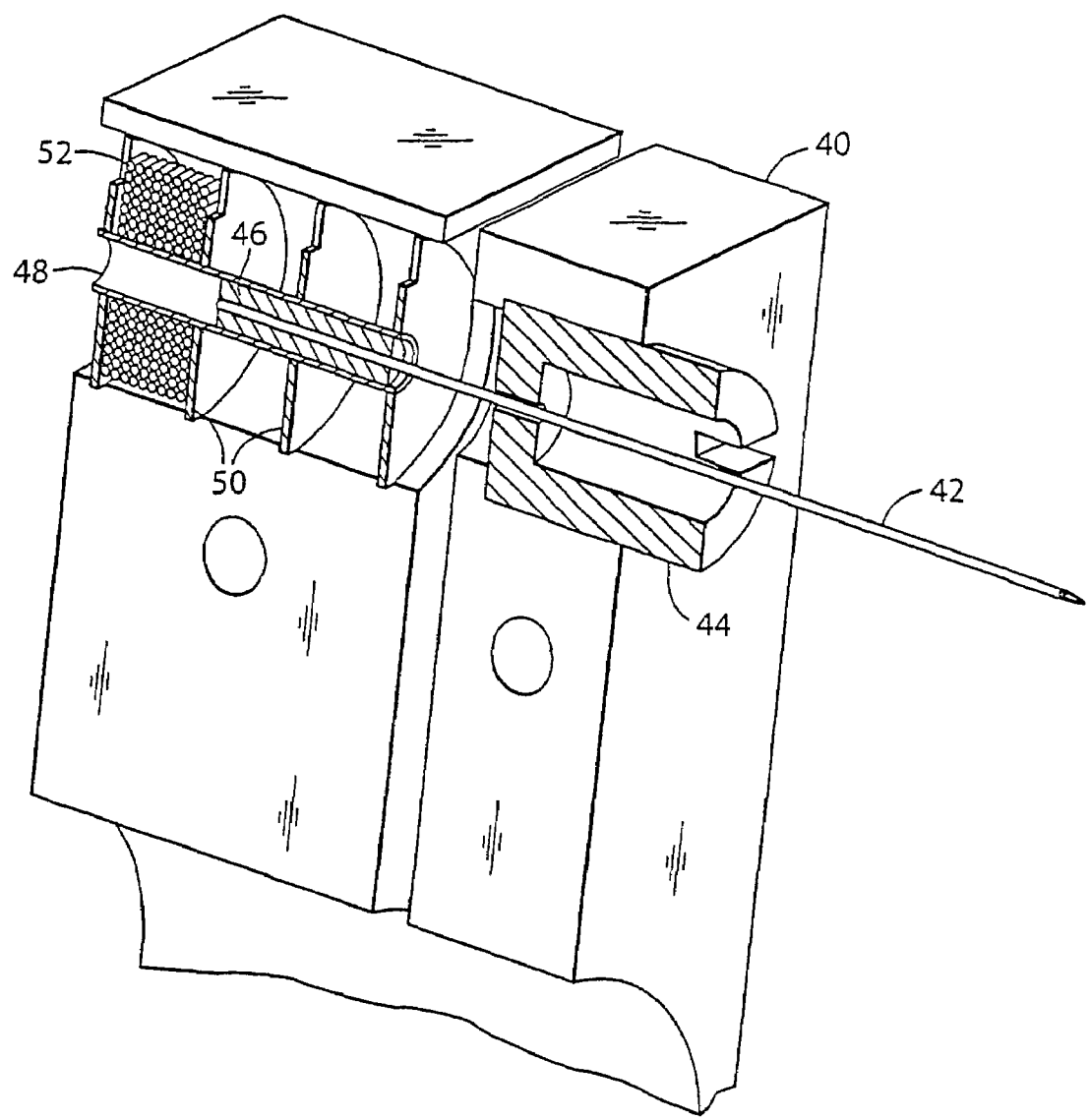
FIG. 3 illustrates a controlled actuator using an electromagnetic actuator to drive the lancet.

Reference will now be made to exemplary embodiments of the invention. In the first embodiment, a lancing device contains a lancet and lancet driver. The lancet and lancet driver are configured so that feedback control is based on lancet displacement, velocity, or acceleration. The feedback control information relating to the actual lancet path is returned to a processor that regulates the energy to the lancet driver, thereby precisely controlling the lancet throughout its advancement and retraction. The lancet driver may be driven by electric current which includes direct current and alternating current. FIG. 3 shows an electromagnetic type lancet driver that is capable of driving an iron core mounted to the lancet assembly using a direct current (DC) power supply. The solenoid is divided into three separate coils along the path of the lancet, two end coils and a middle coil. Direct current is applied to the coils to advance and retract the lancet. The coils are used in pairs to draw the iron core into the solenoid. As one of the drive coils is switched on, the corresponding induced current in the adjacent coil is monitored. The strength of this induced current is related to the degree of magnetic coupling provided by the iron core, and can be used to infer the position of the core. After a period of time, the drive voltage is turned off, allowing the coils to relax, and then the cycle is repeated. The degree of magnetic coupling between the coils is converted electronically to a proportional DC voltage that is supplied to an analog-to-digital converter. The digitized position signal is then processed and compared to a desired "nominal" position by a central processing unit (CPU). Error between the actual and nominal positions is used by the CPU to set the level and/or length of the next power pulse to the solenoid coils.

Referring to FIG. 3, the stationary housing (40) contains the solenoid whose first coil (52) is separated by a magnetically permeable spacer (50) from the adjacent coil. The housing (40) is made from a magnetically permeable material, and a magnetically permeable spacer is assembled outside of the first coil. The spacers and housing form a magnetic circuit that focuses the magnetic field produced by the coil between the inner diameter edges of the spacers. The same is true of each of the other coils, the housing, and their spacers. The inner guide tube (48) isolates the lancet (42) and iron core (46) from the solenoid coils (52). The lancet (42) and iron core (46) are centered by the lancet guide (44).

The lancet (42) is advanced and retracted by alternating the current between the first coil (52), the middle coil (not shown), and the third coil (not shown), singly or in combination, to advance or retract the iron core (46). The lancet guide (44) is also serves as a stop for the iron core (46) mounted to the lancet (42).

In another embodiment, the solenoid comprises three coils consisting of a central driving coil flanked by balanced detection coils built into the driver assembly so that they surround the actuation region with the region centered on the middle coil at mid-stroke. When a current pulse is applied to the central coil, voltages are induced in the adjacent sense coils. If the sense coils are connected together so that their induced voltages oppose each other, the resulting signal will be positive for deflection from mid-stroke in one direction, negative in the other direction, and zero at mid-stroke. This measuring technique is commonly used in Linear Variable Differential Transformers (LVDT). Lancet position is determined by measuring the electrical balance between the two sensing coils.

In another embodiment, the feedback loop uses a commercially available LED/photo transducer module such as the OPB703 (manufactured by Optek Technology, Inc., 1215 W. Crosby Road, Carrollton, Tex., 75006 (972) 323–2200) to determine the distance from the fixed module on the stationary housing to a reflective surface or target mounted on the lancet assembly. The LED acts as a light emitter to send light beams to the reflective surface which in turn reflects the light back to the photo transducer which acts as a light sensor. Distances over the range of 4 mm or so are determined by measuring the intensity of the reflected light by the photo transducer.

In another embodiment, the feed-back loop uses a magnetically permeable region on the lancet shaft itself as the core of a Linear Variable Differential Transformer (LVDT). A permeable region created by selectively annealing a portion of the lancet shaft, or by including a component in the lancet assembly, such as ferrite, with sufficient magnetic permeability to allow coupling between adjacent sensing coils. Coil size, number of windings, drive current, signal amplification, and air gap to the permeable region are specified in the design process.

In another embodiment, the feedback control supplies a piezoelectric driver, superimposing a high frequency oscillation on the basic displacement profile. The piezoelectric driver provides improved cutting efficiency and reduces pain by allowing the lancet to "saw" its way into the tissue or to destroy cells with cavitation energy generated by the high frequency of vibration of the advancing edge of the lancet. The drive power to the piezoelectric driver is monitored for an impedance shift as the device interacts with the target tissue. The resulting force measurement, coupled with the known mass of the lancet is used to determine lancet acceleration, velocity, and position.

Figure 4:
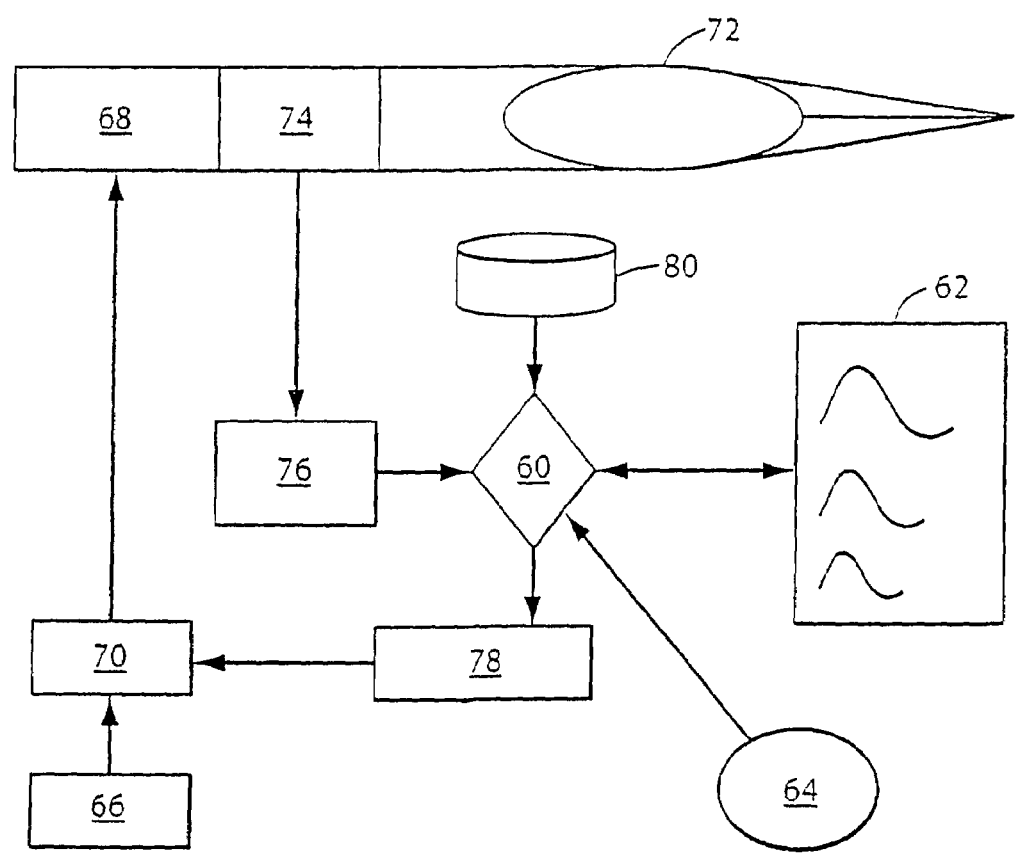
FIG. 4 is a flowchart illustrating a controlled feed-back loop.

FIG. 4 shows the operation of the feedback loop using the processor. The processor (60) stores profiles (62) in non-volatile memory. A user inputs information (64) about the desired circumstances for the lancing event. The processor (60) selects a profile (62) from a set of alternative profiles that have been preprogrammed in the processor (60) based on typical device performance determined through testing at the factory. The processor (60) may customize by either scaling or modifying the profile based on additional user input information (64). Once the processor has chosen and customized the profile, the processor (60) is ready to modulate the power from the power supply (66) to the lancet driver (68) through an amplifier (70). The processor (60) measures the location of the lancet (72) using a position sensing mechanism (74) through an analog to digital converter (76). Examples of position sensing mechanisms have been described in the embodiments above. The processor (60) calculates the movement of the lancet by comparing the actual profile of the lancet to the predetermined profile. The processor (60) modulates the power to the lancet driver (68) through a signal generator (78), which controls the amplifier (70) so that the actual profile of the lancet does not exceed the predetermined profile by more than a preset error limit. The error limit is the accuracy in the control of the lancet.

After the lancing event, the processor (60) allows the user to rank the results of the lancing event. The processor (60) stores these results and constructs a database (80) for the individual user. Using the database (80), the processor (60) calculates the profile traits such as degree of painlessness, success rate, and blood volume for various profiles (62) depending on user input information (64) to optimize the profile to the individual user for subsequent lancing cycles. These profile traits depend on the characteristic phases of lancet advancement and retraction. The processor (60) uses these calculations to optimize profiles (62) for each user. In addition to user input information (64), an internal clock allows storage in the database (80) of information such as the time of day to generate a time stamp for the lancing event and the time between lancing events to anticipate the user's diurnal needs. The database stores information and statistics for each user and each profile that particular user uses.

In addition to varying the profiles, the processor calculates the appropriate lancet diameter and geometry necessary to realize the blood volume required by the user. For example, if the user requires a 1–5 microliter volume of blood, the processor selects a 200 micrometer lancet diameter to achieve these results. For each class of lancet, both diameter and lancet tip geometry, is stored in the processor to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the lancet is varied during advancement and retraction to follow the profile. The method of lancing using the lancing device comprises selecting a profile, lancing, determining lancing profile traits for each characteristic phase of the lancing cycle, and optimizing for subsequent lancing events.

Figure 5:
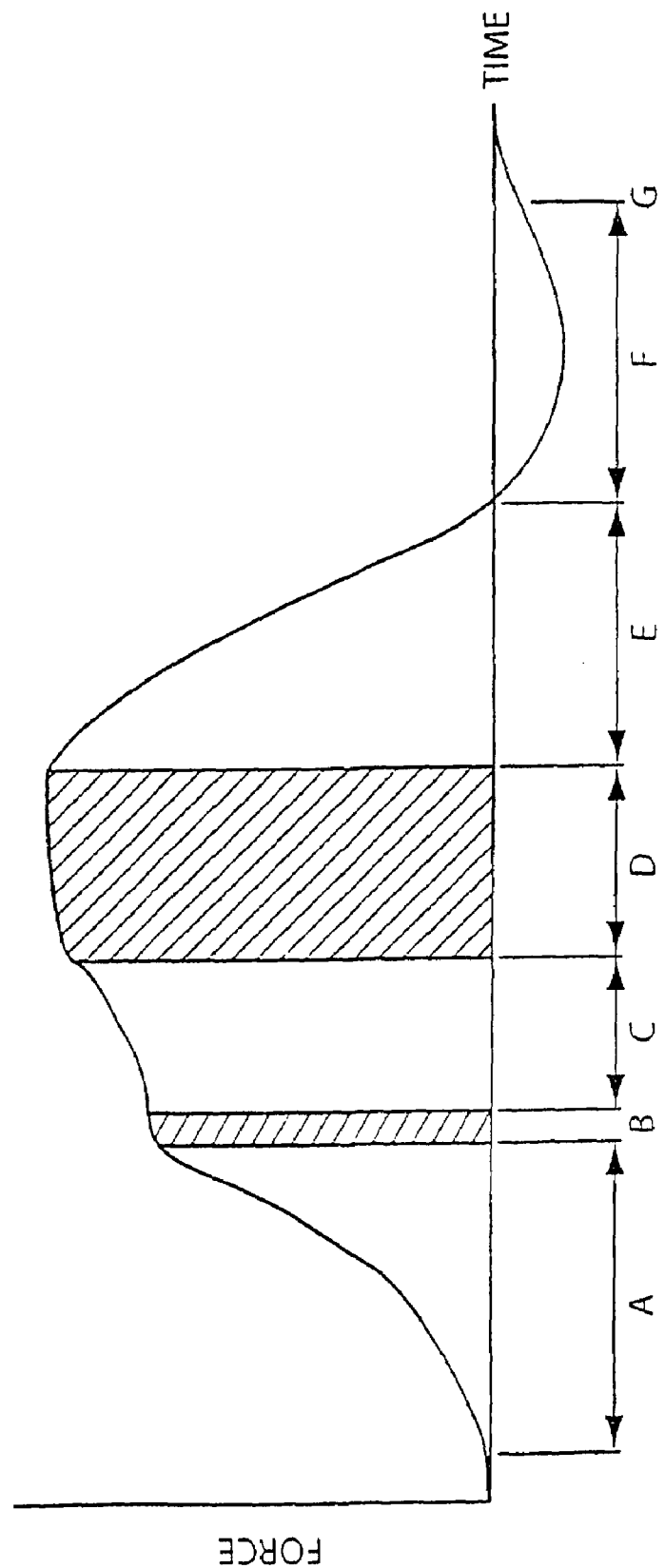
FIG. 5 is a graph of force vs. time during the advancement and retraction of a lancet showing the characteristic phases of the lancing cycle.

FIG. 5 shows the characteristic phases of lancet advancement and retraction on a graph of force versus time illustrating the force exerted by the lancet driver on the lancet to achieve the desired displacement and velocity profile. The characteristic phases are the lancet introduction phase A-C where the lancet is longitudinally advanced into the skin, the lancet rest phase D where the lancet terminates its longitudinal movement reaching its maximum depth and becoming relatively stationary, and the lancet retraction phase E-G where the lancet is longitudinally retracted out of the skin. The duration of the lancet retraction phase E-G is longer than the duration of the lancet introduction phase A-C, which in turn is longer than the duration of the lancet rest phase D.

The introduction phase further comprises a lancet launch phase prior to A when the lancet is longitudinally moving through air toward the skin, a tissue contact phase at the beginning of A when the distal end of the lancet makes initial contact with the skin, a tissue deformation phase A when the skin bends depending on its elastic properties which are related to hydration and thickness, a tissue lancing phase which comprises when the lancet hits the inflection point on the skin and begins to cut the skin B and the lancet continues cutting the skin C. The lancet rest phase D is the limit of the penetration of the lancet into the skin. Pain is reduced by minimizing the duration of the lancet introduction phase A-C so that there is a fast incision to a certain penetration depth regardless of the duration of the deformation phase A and inflection point cutting B which will vary from user to user. Success rate is increased by measuring the exact depth of penetration from inflection point B to the limit of penetration in the lancet rest phase D. This measurement allows the lancet to always, or at least reliably, hit the capillary beds which are a known distance underneath the surface of the skin.

The lancet retraction phase further comprises a primary retraction phase E when the skin pushes the lancet out of the wound tract, a secondary retraction phase F when the lancet starts to become dislodged and pulls in the opposite direction of the skin, and lancet exit phase G when the lancet becomes free of the skin. Primary retraction is the result of exerting a decreasing force to pull the lancet out of the skin as the lancet pulls away from the finger. Secondary retraction is the result of exerting a force in the opposite direction to dislodge the lancet. Control is necessary to keep the wound tract open as blood flows up the wound tract. Blood volume is increased by using a uniform velocity to retract the lancet during the lancet retraction phase E-G regardless of the force required for the primary retraction phase E or secondary retraction phase F, either of which may vary from user to user depending on the properties of the user's skin.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A lancing device comprising:
a lancet with a shaft having a proximal driving end and a distal lancing end;
a lancet driver coupled to said lancet for longitudinal displacement of said lancet; and
a lancet controller coupled to said lancet driver and configured to change a magnitude of force exerted on the lancet during a lancing cycle, said lancet controller including a feedback loop for monitoring a longitudinal displacement and velocity to provide a controlled acceleration of said lancet and for modulating the lancet driver to provide a predetermined tissue lancing profile having characteristic phases for lancet advancement and retraction; and
a position sensor coupled to the lancet and to the lancet controller, the position sensor and the lancet controller configured to measure
a distance from an initialization point to a point of contact of the lancet to a target tissue surface, the lancet being retracted by the driver to the initialization point with a distance to the target tissue being measured and a depth of penetration of the lancet determined.

2. A lancing device according to claim 1 wherein:
said lancet driver comprises a solenoid.

3. A lancing device according to claim 2 wherein:
said solenoid drives the lancet with electric current.

4. A lancing device according to claim 3 wherein:
said lancet controller comprises additional coil segments disposed adjacent to said solenoid for monitoring the lancet displacement.

5. A lancing device according to claim 1 wherein:
said lancet driver including a means for oscillating the lancet to improve the lancet cutting ability.

6. A lancing device according to claim 5 wherein:
said oscillating means includes a piezoelectric driver.

7. A lancing device according to claim 6 wherein:
said lancet controller controllably varies said tissue lancing profile as a function of impedance changes sensed from said piezoelectric driver resulting from said lancet interacting with said tissue.

8. A lancing device according to claim 5 wherein:
said lancet controller comprises a means for sensing a change in lancing pressure to determine the lancet displacement.

9. A lancing device according to claim 1 wherein:
said lancet controller comprises a processor for modulating the lancet driver.

10. A lancing device according to claim 9 wherein:
said processor comprises memory for storage and retrieval of a set of alternative lancing profiles which the processor uses to modulate the lancet driver.

11. A lancing device according to claim 10 wherein:
a user of said lancing device selects the profile desired from the alternative profiles to modulate the lancet.

12. A lancing device according to claim 9 wherein:
said processor optimizes said phases of said tissue lancing profile based on information entered by the user of said lancing device.

13. A lancing device according to claim 9 wherein:
said processor modulates the lancet driver by comparing an actual profile of the lancet to the profile and maintaining a preset error limit between the actual profile and the profile.

14. A lancing device according to claim 9 wherein:
said processor comprises a database for the user.

15. A lancing device according to claim 14 wherein:
said database allows the calculation of statistics for a profile.

16. A lancing device according to claim 9 or 14 wherein:
said processor comprises an internal clock which links the lancing event with a time stamp.

17. A lancing device according to claim 9 wherein:
said processor calculates an appropriate lancet diameter and geometry to collect a blood volume required by the user.

18. A lancing device according to claim 1 wherein:
said feedback loop further comprises a light detecting sensor and a light emitter for monitoring the relative position of said lancet.

19. A lancing device according to claim 1 wherein:
said feedback loop further comprises an electromagnetic sensor for monitoring the relative position of at least one magnetically permeable region disposed on a region of said shaft, said sensor comprising at least one solenoid.

* * * * *